(12) United States Patent
Wilkinson et al.

(10) Patent No.: US 11,857,798 B2
(45) Date of Patent: Jan. 2, 2024

(54) MODIFICATION OF CARDIAC SENSING AND THERAPY

(71) Applicant: Medtronic, Inc., Minneapolis, MN (US)

(72) Inventors: Jeffrey D. Wilkinson, Vadnais Heights, MN (US); Darrell J. Swenson, Lino Lakes, MN (US)

(73) Assignee: Medtronic, Inc., Minneapolis, MN (US)

( * ) Notice: Subject to any disclaimer, the term of this patent is extended or adjusted under 35 U.S.C. 154(b) by 174 days.

(21) Appl. No.: 16/537,025

(22) Filed: Aug. 9, 2019

(65) Prior Publication Data
US 2020/0046988 A1    Feb. 13, 2020

Related U.S. Application Data

(60) Provisional application No. 62/716,798, filed on Aug. 9, 2018.

(51) Int. Cl.
*A61N 1/39* (2006.01)
*A61B 5/08* (2006.01)
(Continued)

(52) U.S. Cl.
CPC .......... *A61N 1/3956* (2013.01); *A61B 5/0816* (2013.01); *A61B 5/1116* (2013.01); *A61B 5/318* (2021.01)

(58) Field of Classification Search
CPC .. A61N 1/3956; A61N 1/3925; A61N 1/3918; A61B 5/0816; A61B 5/1116; A61B 5/318; A61B 5/341
See application file for complete search history.

(56) References Cited

U.S. PATENT DOCUMENTS 5,607,455 A    3/1997  Armstrong
5,954,752 A    9/1999  Mongeon et al.
(Continued)

FOREIGN PATENT DOCUMENTS

WO    2013186560 A1    12/2013
WO    2018026481 A1    2/2018

OTHER PUBLICATIONS

Goyal A, Chhabra L, Sciammarella JC, et al. Defibrillation. [Updated Jan. 28, 2023]. In: StatPearls [Internet]. Treasure Island (FL): StatPearls Publishing; Jan. 2023. Available from: https://www.ncbi.nlm.nih.gov/books/NBK499899/. (Year: 2023).*

(Continued)

*Primary Examiner* — Gary Jackson
*Assistant Examiner* — Alexander M Eisenberg
(74) *Attorney, Agent, or Firm* — Shumaker & Sieffert, P.A.

(57) ABSTRACT

In some examples, a method for controlling delivery of cardiac therapy and cardiac sensing by a medical device system including electrodes for delivering the cardiac therapy may include storing, in a memory of the medical device system, a respective value for each of a plurality of cardiac therapy and/or sensing parameters and, in association with each of a plurality of heart position states, a respective modification of at least one of the cardiac therapy and/or sensing parameters. Such a method also may include determining a current one of the plurality of heart position states of the patient, modifying the at least one cardiac therapy and/or sensing parameter value according to the modification associated with the current heart position state, and controlling the delivery of the cardiac therapy and/or cardiac sensing according to the modified at least one cardiac therapy and/or sensing parameter value.

23 Claims, 12 Drawing Sheets

(51) Int. Cl.
  *A61B 5/11* (2006.01)
  *A61B 5/318* (2021.01)

(56) References Cited

U.S. PATENT DOCUMENTS

| | | | |
|---|---|---|---|
| 7,130,687 B2 | 10/2006 | Cho et al. | |
| 7,643,877 B2 | 1/2010 | Dujmovic, Jr. et al. | |
| 7,972,276 B1* | 7/2011 | Min | A61B 5/1116 600/529 |
| 8,108,035 B1* | 1/2012 | Bharmi | A61B 5/1116 600/509 |
| 8,708,934 B2 | 4/2014 | Skelton et al. | |
| 2002/0082658 A1 | 6/2002 | Heinrich et al. | |
| 2003/0045910 A1 | 3/2003 | Sorenson et al. | |
| 2003/0139780 A1 | 7/2003 | Markowitz et al. | |
| 2003/0212436 A1 | 11/2003 | Brown | |
| 2005/0096703 A1 | 5/2005 | Sanders | |
| 2005/0209647 A1* | 9/2005 | Wanasek | A61N 1/3956 607/5 |
| 2006/0167502 A1* | 7/2006 | Haefner | A61N 1/05 607/4 |
| 2006/0253043 A1* | 11/2006 | Zhang | A61B 5/366 600/512 |
| 2007/0115277 A1* | 5/2007 | Wang | A61B 5/1116 345/419 |
| 2007/0129643 A1* | 6/2007 | Kwok | A61B 5/0816 600/529 |
| 2007/0179539 A1* | 8/2007 | Degroot | A61N 1/39622 607/5 |
| 2007/0225623 A1 | 9/2007 | Freeman | |
| 2008/0188901 A1 | 8/2008 | Sanghera et al. | |
| 2008/0194980 A1 | 8/2008 | Gisolf et al. | |
| 2009/0005827 A1 | 1/2009 | Weintraub et al. | |
| 2010/0010391 A1* | 1/2010 | Skelton | G16H 10/60 600/595 |
| 2010/0198292 A1* | 8/2010 | Honeck | A61N 1/3686 607/27 |
| 2011/0098775 A1 | 4/2011 | Allavatam et al. | |
| 2011/0112419 A1 | 5/2011 | Björling et al. | |
| 2011/0201945 A1 | 8/2011 | Li et al. | |
| 2012/0109244 A1 | 5/2012 | Anderson et al. | |
| 2012/0259183 A1 | 10/2012 | Thakur et al. | |
| 2013/0289649 A1 | 10/2013 | Averina et al. | |
| 2014/0277256 A1 | 9/2014 | Osorio | |
| 2014/0330326 A1 | 11/2014 | Thompson-Nauman et al. | |
| 2015/0297903 A1 | 10/2015 | Kantor et al. | |
| 2016/0000350 A1 | 1/2016 | Zhang | |
| 2016/0022166 A1 | 1/2016 | Stadler et al. | |
| 2016/0023013 A1 | 1/2016 | Greenhut et al. | |
| 2016/0144192 A1* | 5/2016 | Sanghera | A61N 1/059 607/18 |
| 2017/0027527 A1 | 2/2017 | Bhat et al. | |
| 2017/0056669 A1* | 3/2017 | Kane | A61N 1/36585 |
| 2017/0157395 A1* | 6/2017 | Thompson-Nauman | A61N 1/3925 |
| 2017/0245794 A1 | 8/2017 | Sharma et al. | |
| 2017/0296086 A1 | 10/2017 | Ternes et al. | |
| 2017/0361107 A1* | 12/2017 | McSpadden | A61N 1/371 |
| 2018/0021570 A1 | 1/2018 | An et al. | |
| 2018/0035898 A1 | 2/2018 | Gunderson | |
| 2018/0177425 A1 | 6/2018 | Stadler et al. | |
| 2018/0361162 A1* | 12/2018 | Ternes | A61N 1/36592 |

OTHER PUBLICATIONS

International Preliminary Report on Patentability from International Application No. PCT/US2019/045922, dated Feb. 18, 2021, 6 pp.
Shin et al., "Rate-adaptive pacemaker controlled by motion and respiratory rate using neuro-fuzzy algorithm," Medical & Biological Engineering & Computing, vol. 39, Jul. 3, 2001, 6 pp.
Baudoin et al.,"The superior epigastric artery does not pass through Larrey's space (trigonum sternocostale)," Surgical & Radiologic Anatomy, Springer, published online Aug. 1, 2003, 5 pp.
Wilkinson et al., "Extravascular sensed signal amplitude variability due to posture and respiration: insights from posture specific modeling in a highly automated electrophysiological modeling environment," Best Posters in heart and vascular development / Best Posters in computer modelling and simulation, published Aug. 28, 2018, 1 pp.
International Search Report and Written Opinion of International Application No. PCT/US2019/045922, dated Nov. 5, 2019, 11 pp.
U.S. Appl. No. 16/536,979, filed Aug. 9, 2019, by Thompson-Nauman et al.

* cited by examiner

MODIFICATION OF CARDIAC SENSING AND THERAPY

This application claims the benefit of U.S. Provisional Patent Application No. 62/716,798, filed Aug. 9, 2018, the entire content of which is incorporated by reference herein.

TECHNICAL FIELD

The disclosure relates generally to medical device systems and, more particularly, cardiac sensing and therapy delivery by medical device systems.

BACKGROUND

Some types of implantable medical device (IMD) systems, such as cardiac pacemaker or implantable cardioverter defibrillator systems, may be used to provide cardiac sensing and therapy for a patient via one or more electrodes. Some IMDs include an implantable housing that encloses a pulse generator and other electronic components, which may be configured to be implanted subcutaneously in the chest of the patient, as an example. The IMD may be connected to one or more implantable medical electrical leads that include one or more electrodes. The leads may be configured such that the electrodes may, as examples, be implanted within the heart, e.g., transvenous leads, or outside of the heart and vasculature, e.g., extravascular leads. Extravascular leads of such IMD systems may be configured such that the electrodes, e.g., located on a distal portion of the lead, is implanted subcutaneously, substernally, or in other extravascular locations.

SUMMARY

In some examples, this disclosure is directed to techniques for controlling the delivery of cardiac therapy (e.g., anti-tachyarrhythmia shock therapy and/or cardiac pacing) and cardiac sensing by a medical device, such as an IMD. Some such techniques may include storing values for cardiac therapy and/or sensing parameters, and storing, in association with each of a plurality of heart position states, a respective modification of at least one of the parameters. The heart position states may be states of the patient that likely correspond to different positions of the patient's heart relative to other anatomical structures and/or the electrodes used by a medical device system for cardiac sensing and/or therapy. The heart positions states may change based on one or more factors, such as the patient's posture or respiration state. Accordingly, the heart position states may be defined by one or both of a posture or respiration state.

Such techniques may further include determining a current heart position state of the patient's heart, modifying a cardiac therapy or sensing parameter value according to a modification associated with the patient's current heart position state, and controlling the medical device to deliver cardiac therapy and/or perform cardiac sensing according to the modified cardiac therapy parameter. Example parameters include a cardiac pacing magnitude (e.g., a pulse amplitude or width), an anti-tachyarrhythmia shock magnitude (e.g., a pulse amplitude, pulse width, and/or shock energy), or cardiac electrogram sensing parameter, such as a threshold amplitude for detecting an R-wave, P-wave, or other feature of the cardiac electrogram. In some examples, the parameter is a tachyarrhythmia detection parameter, which may be a cardiac electrogram sensing parameter used to detect tachyarrhythmia. In some examples, the parameter is an electrode vector used to sense a cardiac electrogram and/or deliver cardiac therapy via the modified electrode vector.

IMD systems that utilize transvenous leads may not be a preferred IMD system for all patients. For example, some patients may not be ideal candidates for placement of transvenous leads, such as patients with difficult vascular access, children, and other younger patients. Moreover, transvenous leads may become fibrosed in the heart over time, making lead revision and extraction procedures challenging. Extravascular IMD systems may eliminate the need to implant transvenous leads within the heart. Thus, an extravascular IMD system may be preferred for use in patients for whom a transvenous IMD is not preferred.

In some extravascular IMD systems, the lead(s) may be implanted subcutaneously, substernally, or in other extravascular locations. For example, an extravascular lead may be implanted at least partially in a substernal space, such as at a target site between a ribcage or sternum and a heart of a patient. Such lead positioning may enable an IMD connected to the lead to sense cardiac electrical signals and deliver cardiac therapy, such as pacing pulses and/or anti-tachyarrhythmia shock therapy, to the patient's heart via electrodes on the lead. For example, the extravascular lead may be implanted such that the electrodes on the lead are positioned relative to target locations of the patient's heart, such as relative to one or more chambers of the patient's heart. In this manner, energy delivered via the electrodes during delivery of cardiac therapy may be delivered to the target locations.

In some examples, however, movement of the patient's heart relative to the electrodes of an extravascular lead may change the efficacy and/or efficiency of cardiac sensing and/or therapy by the medical device. For example, in some patients, the heart may move within the patient's chest when the patient changes posture (e.g., from a supine or other lying posture to an upright position) due to the force of gravity, and/or in certain respiratory states (e.g., upon inhalation, deep breathing, and/or rapid breathing). For example, the patient's heart may move caudally when the patient transitions from lying down to a standing position, and/or when the patient inhales. In younger patients, the heart may pivot upon standing and/or inhalation. In any such examples, movement of the heart relative to the electrodes of an IMD may affect one or more of the cardiac sensing and/or cardiac therapy delivery functions of the IMD. For example, a sensed cardiac electrical signal may vary in amplitude and/or morphology as the heart moves, which may result in reduced sensing specificity. During delivery of pacing pulses, movement of the heart may result in the site of capture moving around on the heart, such that the distance between the heart and pacing electrodes on the lead varies. During delivery of antitachyarrhythmia shock therapy, movement of the heart may result in an electrode on the lead (e.g., a most-superior or most-distal electrode) contributing little of the current that flows through the heart upon delivery of the shock therapy. In any such examples, one or more of an efficiency and/or efficacy of the cardiac therapy delivered by the IMD may be reduced at times when the heart is further from the lead relative to times when the heart is closer to the lead.

Thus, it may be desirable to modify cardiac sensing and/or cardiac therapy delivery by the IMD to account for changes in the position of the patient's heart, such as the changes in position that may be associated with posture and/or respiration of the patient. For example, it may be desirable to modify sensing of a cardiac electrical signal via sensing electrodes of the IMD by adjusting a sensing threshold (e.g., an amplitude threshold), an arrhythmia detection parameter, and/or a blanking protocol based on a current position of a patient's heart. Such modification of values of parameters by which the IMD senses the cardiac signal may improve the specificity of arrhythmia detection by the IMD when the heart is in one or more particular positions.

In some examples, it may be desirable to modify delivery of cardiac pacing pulses and/or an anti-tachyarrhythmia shock by the IMD, such as by a magnitude and/or the timing of the delivery of the pacing pulses and/or the anti-tachyarrhythmia shock based on a current position of a patient's heart. Additionally, or alternatively, it may be desirable to modify an electrode vector for cardiac sensing or the delivery of cardiac therapy by the IMD based on a current position of the patient's heart. In any such examples, modifying cardiac sensing and/or cardiac therapy delivery by the IMD to account for changes in the position of the patient's heart may enable more efficient and/or effective delivery of cardiac therapy by the IMD when the heart is in certain positions. Accordingly, some techniques described herein may include modifying cardiac sensing and/or delivery of cardiac therapy (e.g., cardiac pacing and/or anti-tachyarrhythmia shock therapy) by a medical device system.

In one example, the disclosure is directed to a method storing, in a memory of a medical device system, a respective value for each of a plurality of parameters for at least one of anti-tachyarrhythmia shock therapy or cardiac sensing, and, in association with each of a plurality of heart position states, a respective modification of at least one of the plurality of parameters; and by processing circuitry of the medical device system: determining a current one of the plurality of heart position states of a patient, modifying the at least parameter value according to the modification associated with the current heart position state; and controlling at least one of the delivery of the anti-tachyarrhythmia shock therapy or the cardiac sensing according to the modified at least one parameter value.

In another example, the disclosure is directed to a medical device system comprising a plurality of electrodes; a memory configured to store a respective value for each of a plurality of parameters for at least one of anti-tachyarrhythmia shock therapy or cardiac sensing, and, in association with each of a plurality of heart position states, a respective modification of at least one of the plurality of parameters; and processing circuitry configured to: determine a current one of the plurality of heart position states of the patient; modify the at least one parameter value according to the modification associated with the current heart position state; and control at least one of the delivery of the anti-tachyarrhythmia shock therapy or the cardiac sensing via the plurality of electrodes according to the modified at least one parameter value.

In another example, the disclosure is directed to a method for controlling cardiac electrogram sensing or delivery of cardiac therapy by an implantable medical device system comprising a plurality of electrodes, the method comprising, by processing circuitry of the medical device system: determining a heart position state of the patient; modifying a vector comprising at least two of the plurality of electrodes based on the determined heart position state; and controlling the medical device system to at least sense a cardiac electrogram or deliver cardiac therapy via the modified vector comprising the at least two of the plurality of electrodes.

In another example, the disclosure is directed to a medical device system for controlling cardiac electrogram sensing or delivery of cardiac therapy, the system comprising, a plurality of electrodes; and processing circuitry configured to: determine a heart position state of the patient; modify a vector comprising at least two of the plurality of electrodes based on the determined heart position state; and control the medical device system to at least sense a cardiac electrogram or deliver cardiac therapy via the modified vector comprising the at least two of the plurality of electrodes.

This summary is intended to provide an overview of the subject matter described in this disclosure. It is not intended to provide an exclusive or exhaustive explanation of the methods and systems described in detail within the accompanying drawings and description below. The details of one or more aspects of the disclosure are set forth in the accompanying drawings and the description below.

BRIEF DESCRIPTION OF DRAWINGS

The details of one or more examples of this disclosure are set forth in the accompanying drawings and the description below. Other features, objects, and advantages of this disclosure will be apparent from the description and drawings, and from the claims.

DETAILED DESCRIPTION

Figure 1A:
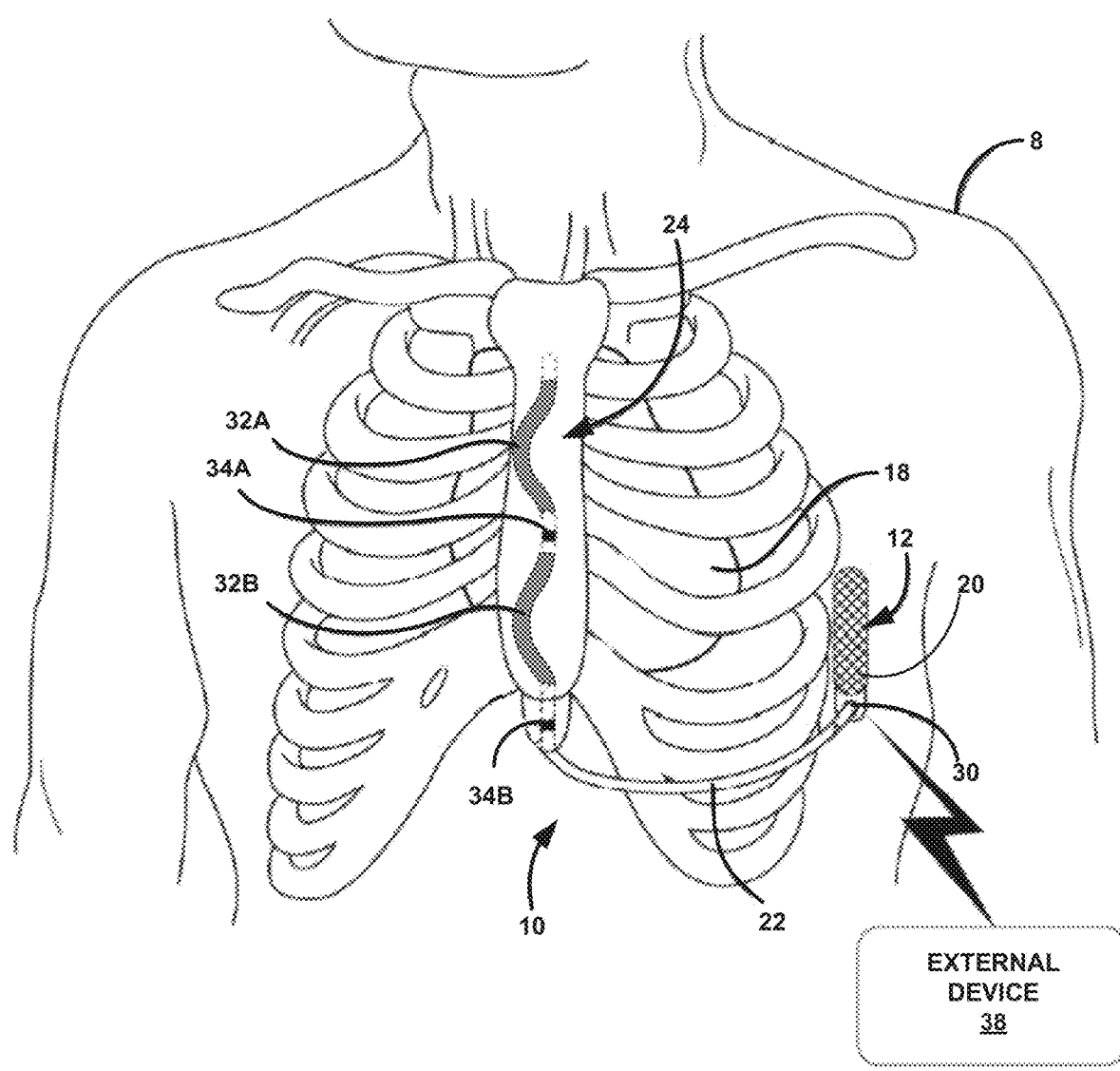
FIG. 1A is a conceptual drawing illustrating a front view of a patient with an example medical device system having a substernal lead.

In some examples, this disclosure describes example techniques related to controlling the sensing of cardiac electrical signals and/or the delivery of cardiac therapy (e.g., cardiac pacing or anti-tachyarrhythmia shocks) by a medical device system based on a current heart position state of the patient. In some examples, processing circuitry of a medical device or other processing circuitry of the medical device system, may determine a current heart position state of the patient of a plurality of heart position states stored in a memory of the medical device system and in association with a respective modification of at least one of a plurality of cardiac therapy and/or sensing parameters. According to some example techniques described herein, the processing circuitry also may modify the at least one cardiac therapy or sensing parameter value according to the modification associated with the current heart position state, and control the delivery of the cardiac therapy according to the modified at least one cardiac therapy parameter value. In some examples, the processing circuitry may modify an electrode vector that includes at least two of a plurality of electrodes of the medical device system, based on the current heart position state, and control the medical device system to at least sense a cardiac electrogram or deliver cardiac therapy via the modified electrode vector.

Each of the heart position states may be associated with one or more postures of the patient in a memory of the medical device system. For example, a heart position state in which the heart is more caudal (e.g., relative to a baseline position) may be associated to a sitting, standing, or otherwise upright posture. Thus, the processing circuitry may determine the current heart position state of the patient by determining a current posture of the patient. Additionally, or alternatively, each of the heart position states may be associated with a respiratory state of the patient, such as at least one of an inhalation phase, a respiratory rate, or a respiratory depth of the patient. For example, a heart position state in which the heart is more caudal, relative to a baseline position, may be associated with one or more of an inhalation phase, an elevated respiratory rate, and/or an increased respiratory depth (e.g., relative to baseline or other threshold respiration values). In such examples, the processing circuitry may determine a respiratory state of the patient based on signals received by one or more sensors of the medical device system, as discussed below with respect to FIGS. 1A-2. In some examples, the processing circuitry may further determine that the respiratory state of the patient is at least one of an inhalation phase, a respiratory depth satisfying a respiratory depth threshold, or a respiratory rate satisfying a respiratory rate threshold.

In examples in which the processing circuitry determines the current heart position state based on both a posture and a respiratory state, the determined posture and the determined respiratory state, taken together, may be associated with a different heart position state than if taken separately. For example, when the patient is in an upright posture and breathing deeply, the processing circuitry may determine that the patient's heart position state is different (e.g., because the heart may be more caudal) than when the patient is upright but not breathing deeply or lying down and breathing deeply.

To adapt cardiac therapy to the patient's heart position state, the processing circuitry may modify the at least one cardiac therapy parameter value according to a modification associated with the patient's current heart position state by modifying a tachyarrhythmia detection parameter. For example, the tachyarrhythmia detection parameter may be a threshold heart rate (e.g., a certain number of beats per minute over a baseline heart rate) that, if satisfied, may indicate a tachyarrhythmia. However, the patient may have a different (e.g., higher) baseline heart rate during inhalation than during exhalation. If the tachyarrhythmia detection threshold is not adjusted to account for this difference in baseline heart rate during inhalation and exhalation, a false-positive detection of tachyarrhythmia may occur during inhalation. Thus, the processing circuitry may modify the tachyarrhythmia detection threshold by increasing the threshold when the patient's heart position state corresponds to inhalation, which may improve an accuracy of tachyarrhythmia detection during inhalation and reduce a possibility of delivering unnecessary anti-tachyarrhythmia shocks, which may be uncomfortable for the patient or may unnecessarily deplete a power source of the medical device system. Other examples of tachyarrhythmia detection parameters that may be modified based on the heart position state include an amplitude threshold of the cardiac electrogram used to detect features, such as R-waves or P-waves, of the cardiac electrogram, or a cardiac electrogram morphology parameter, such as template used to distinguish treatable tachyarrhythmias from other tachyarrhythmias (e.g., supra-ventricular tacharrhythmias).

In some examples, the processing circuitry may modify the at least one cardiac therapy parameter value according to the modification associated with the patient's current heart position state by modifying a cardiac electrogram sensing parameters, such as an amplitude threshold. For example, a baseline cardiac electrogram sensing amplitude threshold may be selected to enable sensing of a desired portion of a sensed cardiac electrogram (e.g., an R-wave), when one or more sensing electrodes are positioned approximately over a target portion of the heart such as a ventricle. However, when the patient's heart position is caudal to a baseline position, such as when the patient is upright and/or inhaling, the one or more other portions of the sensed electrogram (e.g., a T-wave) may be more prominent. In some such examples, oversensing of a T-wave may result in an increased possibility of a false-positive detection of tachyarrhythmia. Thus, it may be beneficial to increase a sensing threshold amplitude associated with such other portions of the cardiac electrogram to reduce a possibility of false-positive tachyarrhythmia detection. For example, the processing circuitry may modify the cardiac electrogram sensing amplitude threshold by increasing a cardiac electrogram sensing amplitude threshold when the patient's heart position is more caudal. In some examples, modifying the cardiac electrogram sensing threshold improve an accuracy of tachyarrhythmia detection during inhalation, which may reduce a possibility of delivering unnecessary anti-tachyarrhythmia shocks that may be uncomfortable for the patient or may unnecessarily deplete a power source of the medical device system.

In some examples, the processing circuitry may modify the at least one cardiac therapy parameter value according to the modification associated with the patient's current heart position state by modifying an anti-tachyarrhythmia shock or pacing pulse magnitude (which may be a pulse amplitude, width, or energy). For example, a baseline anti-tachyarrhythmia shock or pacing pulse magnitude may be selected to effectively treat a tachyarrhythmia or maintain pacing capture when one or more defibrillation or pacing electrodes are positioned approximately over the heart. However, when the patient's heart position is caudal to a baseline position, such as when the patient is upright and/or inhaling, one or more of the defibrillation or pacing electrodes may no longer be positioned approximately over the heart. In some examples, such movement of the heart away from the electrodes may reduce an efficacy of an anti-tachyarrhythmia shock or may result in loss of pacing capture. In such examples, the processing circuitry may modify the cardiac therapy parameter by increasing an anti-tachyarrhythmia shock magnitude or increasing an amplitude of one or more pacing pulses when the patient's heart position state corresponds to one or more postures or respiratory states associated with a more caudal (e.g., relative to a baseline) heart position. By accounting for the movement of the patient's heart relative to the defibrillation or pacing electrodes, the medical device system may deliver effective anti-tachyarrhythmia shock therapy or maintain pacing capture even when the heart moves away from the electrodes.

In some examples in which the processing circuitry may modify the at least one cardiac therapy parameter value according to a modification associated with a patient's current heart position state, the anti-tachyarrhythmia shock therapy parameters may be a sensing vector that includes at least two of a plurality of electrodes of a lead coupled to the medical device and a shock vector that includes the at least two of the plurality of electrodes. As discussed above, when the patient's heart position is caudal to a baseline position, one or more electrodes (e.g., sensing and/or defibrillation electrodes) positioned on a lead may no longer be approximately over the heart. In such examples, the processing circuitry may account for the position of the heart by removing one or more of the electrodes not positioned approximately over the heart from the electrode vector, as such electrodes may not be positioned to deliver sufficient energy to the heart or sense cardiac electrical signals when the heart is more caudal. For example, the one or more electrodes removed from the sensing vector or the shock vector may be one or more electrodes positioned on a distal portion of the lead. In some examples, an anti-tachyarrhythmia shock delivered by the medical device using such a modified shock vector may improve an efficacy of anti-tachyarrhythmia shock therapy, such as by increasing shock impedance and more efficiently directing and sustaining delivery of energy to the heart via the electrodes of the modified shock vector.

In some techniques in which the processing circuitry may control the medical device system to at least sense a cardiac electrogram or deliver cardiac therapy via a modified electrode vector, the processing circuitry may control the medical device system to deliver cardiac therapy by controlling the medical device system to deliver cardiac pacing via the modified vector. As discussed above, when the patient's heart is positioned caudal to a baseline position one or more of electrodes positioned on a lead (e.g., sensing and/or pacing electrodes positioned on a distal portion of the lead) may no longer be positioned approximately over a portion of the heart to which it may be desirable to deliver pacing pulses, such as a ventricle. Instead, for example, one or more of the electrodes may be positioned over an atrium of the heart when the heart is position is caudal to a baseline position. Pacing pulses delivered via one or more electrodes positioned over a non-target portion of the heart may not contribute to pacing efficacy and may reduce energy efficiency of the medical device system. Thus, it may be desirable to remove such electrodes from a pacing vector when the heart is positioned more caudal to improve pacing efficiency.

In any of the example techniques described herein, the modifications to the cardiac therapy or sensing parameters and/or electrode vectors may be selected by a clinician and programmed into a memory of the medical device system. Such modifications may be selected for an individual patient, as an amount and/or direction of that a patient's heart may move with changes in posture and/or respiration may vary between patients. Thus, the clinician may select the modifications based on a magnitude and/or direction of movement of a particular patient's heart with changes in patient posture and/or respiration. For example, patients with smaller hearts (e.g., younger and/or female patients) may have less heart movement than patients with larger hearts (e.g., older and/or male patients). In some examples, hearts of younger patients may pivot with changes in posture and/or respiration. Thus, the clinician may select the modifications based on one or more of a gender, age, or size (e.g., height and/or weight) of the patient.

In some examples, the clinician may directly observe (e.g., via fluoroscopy) an amount and/or direction of movement of the patient's heart with changes in posture and/or respiration. In such examples, the medical device system may automatically or semi-automatically modify values of one or more cardiac therapy parameters, cardiac sensing parameters, or electrode vectors as the patient's heart moves with changes in patient posture and/or respiration. Thus, the techniques described herein may improve the efficacy and efficiency of the cardiac therapy delivery by more accurately directing energy to target portions of the heart and by reducing the delivery of energy to non-target locations.

A medical device of a medical device system used in some of the example techniques may be an IMD configured for implantation within the patient, such as substernally or subcutaneously, and may be configured to sense cardiac electrical signals and deliver cardiac therapy via at least one electrode of the IMD. In other examples, a medical device of a medical device system used in some of the example techniques may be an external medical device (e.g., not configured for implantation within the patient) configured to sense cardiac electrical signals and deliver anti-tachyarrhythmia shocks via at least one electrode of the medical device.

Figure 1B:
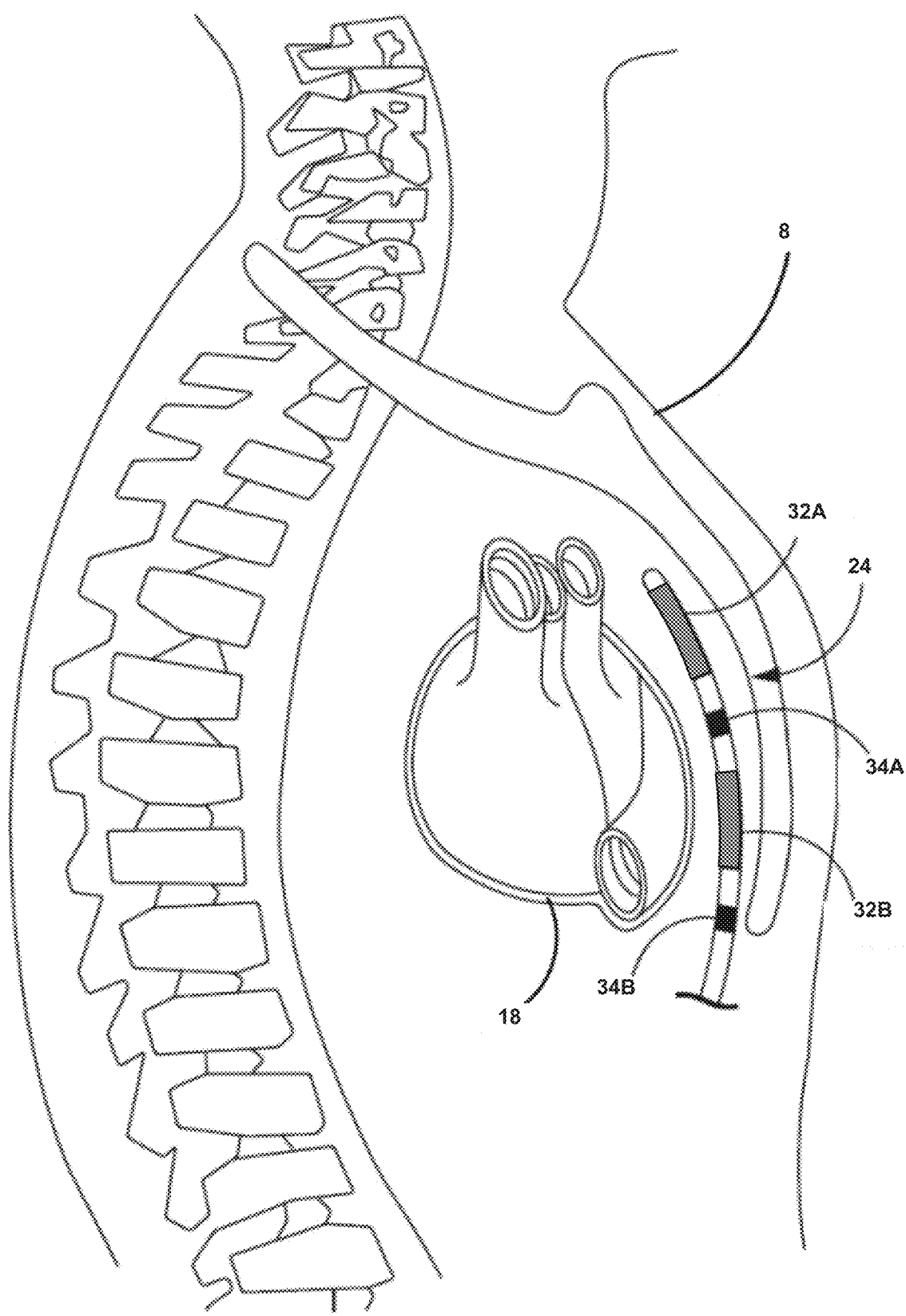
FIG. 1B is a conceptual drawing illustrating a side view of the patient with the example medical device system of FIG. 1A.
Figure 1C:
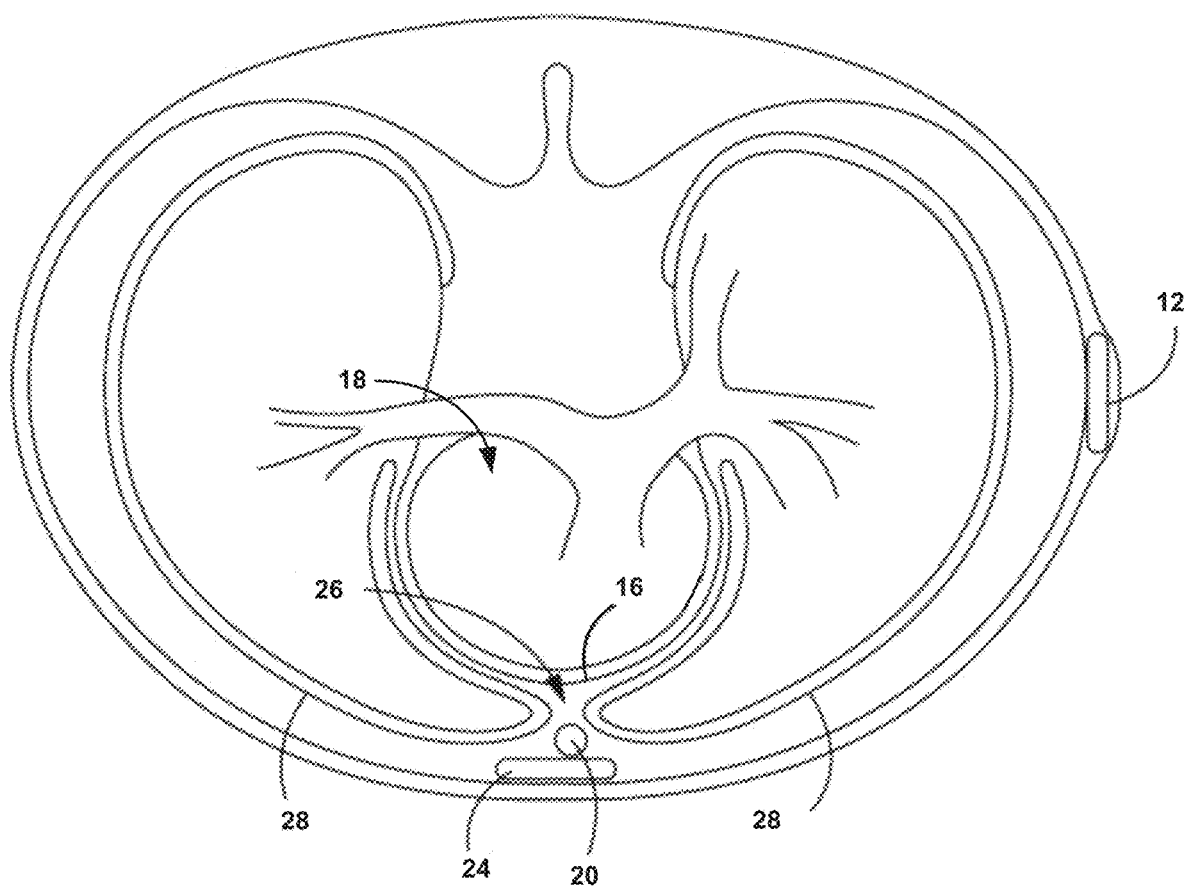
FIG. 1C is a conceptual drawing illustrating a transverse view of the patient with the example medical device system of FIG. 1A.

FIGS. 1A-1C are conceptual diagrams of a medical device system 10 implanted within a patient 8. FIG. 1A is a front view of medical device system 10 implanted within patient 8. FIG. 1B is a side view of medical device system 10 implanted within patient 8. FIG. 1C is a transverse view of medical device system 10 implanted within patient 8.

In some examples, the medical device system 10 is an extravascular implantable cardioverter-defibrillator (EV-ICD) system implanted within patient 8. However, the techniques described herein may be applicable to other implanted and/or external cardiac systems, including cardiac pacemaker systems, cardiac resynchronization therapy defibrillator (CRT-D) systems, cardioverter systems, wearable automated external defibrillator (WAED) systems, or combinations thereof, as well as other stimulation and/or sensing systems, such as neurostimulation systems. In addition, system 10 may not be limited to treatment of a human patient. In alternative examples, system 10 may be implemented in non-human patients, such as primates, canines, equines, pigs, bovines, ovines, felines, or the like. These other animals may undergo clinical or research therapies that may benefit from the subject matter of this disclosure.

IMD 12 is configured to be implanted in a patient, such as patient 8. In some examples, IMD 12 is implanted subcutaneously or submuscularly on the left midaxillary of patient 8, such that IMD 12 may be positioned on the left side of patient 8 above the ribcage. In some other examples, IMD 12 may be implanted at other subcutaneous locations on patient 8 such as at a pectoral location or abdominal location. IMD 12 includes housing 20 that may form a hermetic seal that protects components of IMD 12. In some examples, housing 20 of IMD 12 may be formed of a conductive material, such as titanium, or of a combination of conductive and nonconductive materials, which may function as a housing electrode. IMD 12 may also include a connector assembly (also referred to as a connector block or header) that includes electrical feedthroughs through which electrical connections are made between lead 22 and electronic components included within the housing. Housing 20 may house one or more of processing circuitry, memories, transmitters, receivers, sensors, sensing circuitry, therapy circuitry, power sources and other appropriate components.

In general, medical device systems (e.g., system 10) may include one or more medical devices, leads, external devices, or other components configured to implement the techniques described herein. In the illustrated example, IMD 12 is connected to at least one implantable cardiac lead 22. In other examples, two leads may be used. In some examples, IMD 12 may be configured to deliver high-energy anti-tachyarrhythmia (e.g., cardioversion or defibrillation) shocks to patient's heart 18 when a ventricular tachyarrhythmia, e.g., ventricular tachycardia (VT) or ventricular fibrillation (VF), is detected. Cardioversion shocks are typically delivered in synchrony with a detected R-wave when fibrillation detection criteria are met. Defibrillation shocks are typically delivered when fibrillation criteria are met, and the R-wave cannot be discerned from signals sensed by IMD 12.

Lead 22 includes an elongated lead body having a proximal end that includes a connector (not shown) configured to be connected to IMD 12 and a distal portion that includes electrodes 32A, 32B, 34A, and 34B. Lead 22 extends subcutaneously above the ribcage from IMD 12 toward a center of the torso of patient 8. At a location near the center of the torso, lead 22 bends or turns and extends intrathoracically superior under/below sternum 24. Lead 22 thus may be implanted at least partially in a substernal space, such as at a target site between the ribcage or sternum 24 and heart 18. In one such configuration, a proximal portion of lead 22 may be configured to extend subcutaneously from IMD 12 toward sternum 24 and a distal portion of lead 22 may be configured to extend superior under or below sternum 24 in the anterior mediastinum 26 (FIG. 1C). Lead 22 may include one or more curved sections as discussed herein to configure lead 22 to naturally (e.g., in a self-biasing manner) extend in this way upon deployment.

For example, lead 22 may extend intrathoracically superior under/below sternum 24 within anterior mediastinum 26. Anterior mediastinum 26 may be viewed as being bounded posteriorly by pericardium 16, laterally by pleurae 28, and anteriorly by sternum 24. In some examples, the anterior wall of anterior mediastinum 26 may also be formed by the transversus thoracis and one or more costal cartilages. Anterior mediastinum 26 includes a quantity of loose connective tissue (such as areolar tissue), some lymph vessels, lymph glands, substernal musculature (e.g., transverse thoracic muscle), and small vessels or vessel branches. In one example, the distal portion of lead 22 may be implanted substantially within the loose connective tissue and/or substernal musculature of anterior mediastinum 26. In such examples, the distal portion of lead 22 may be physically isolated from pericardium 16 of heart 18. A lead implanted substantially within anterior mediastinum 26 will be referred to herein as a substernal lead. Electrical stimulation, such as anti-arrhythmia pacing, cardioversion or defibrillation, provided by lead 22 implanted substantially within anterior mediastinum 26 may be referred to herein as substernal electrical stimulation, substernal pacing, impedance monitoring, substernal cardioversion, or substernal defibrillation.

The distal portion of lead 22 is described herein as being implanted substantially within anterior mediastinum 26. Thus, some of distal portion of lead 22 may extend out of anterior mediastinum 26 (e.g., a proximal end of the distal portion), although much of the distal portion may be positioned within anterior mediastinum 26. In other embodiments, the distal portion of lead 22 may be implanted intrathoracically in other non-vascular, extra-pericardial locations, including the gap, tissue, or other anatomical features around the perimeter of and adjacent to, but not attached to, the pericardium 16 or other portion of heart 18 and not above sternum 24 or the ribcage. As such, lead 22 may be implanted anywhere within the "substernal space" defined by the undersurface between the sternum and/or ribcage and the body cavity but not including pericardium 16 or other portions of heart 18. The substernal space may alternatively be referred to by the terms "retrosternal space" or "mediastinum" or "infrasternal" as is known to those skilled in the art and includes the anterior mediastinum 26. The substernal space may also include the anatomical region described in Baudoin, Y. P., et al., entitled "The superior epigastric artery does not pass through Larrey's space (trigonum sternocostale)." Surg.Radiol.Anat. 25.3-4 (2003): 259-62 as Larrey's space. In other words, the distal portion of lead 22 may be implanted in the region around the outer surface of heart 18, but not attached to heart 18. For example, the distal portion of lead 22 may be physically isolated from pericardium 16.

Lead 22 may include an insulative lead body having a proximal end that includes connector 30 configured to be connected to IMD 12 and a distal portion that includes one or more electrodes. As shown in FIG. 1A, the one or more electrodes of lead 22 may include electrodes 32A, 32B, 34A, and 34B, although in other examples, lead 22 may include more or fewer electrodes. Lead 22 also includes one or more conductors that form an electrically conductive path within the lead body and interconnect the electrical connector and respective ones of the electrodes.

Electrodes 32A, 32B may be defibrillation electrodes (individually or collectively "defibrillation electrode(s) 32"). Although electrodes 32 may be referred to herein as "defibrillation electrodes 32," electrodes 32 may be configured to deliver other types of anti-tachyarrhythmia shocks, such as cardioversion shocks. In some examples, defibrillation electrodes 32A, 32B may functionally be different sections of a single defibrillation electrode 32, such that both defibrillation electrodes 32 are coupled to the same conductor or are otherwise configured to provide the same electrical stimulation. Though defibrillation electrodes 32 are depicted in FIGS. 1A-IC as coil electrodes for purposes of clarity, it is to be understood that defibrillation electrodes 32 may be of other configurations in other examples, such as an elongated coil electrode. Defibrillation electrodes 32 may be located on the distal portion of lead 22, where the distal portion of lead 22 is the portion of lead 22 that is configured to be implanted as extending along the sternum 24.

Lead 22 may be implanted at a target site below or along sternum 24 such that a therapy vector is substantially across a ventricle of heart 18. In some examples, a therapy vector (e.g., a shock vector for delivery of anti-tachyarrhythmia shock) may be between defibrillation electrodes 32 and a housing electrode formed by or on IMD 12, as discussed further below. The therapy vector may, in one example, be viewed as a line that extends from a point on defibrillation electrodes 32 (e.g., a center of one of the defibrillation electrodes 32) to a point on a housing electrode of IMD 12. As such, it may be advantageous to increase an amount of area across which defibrillation electrodes 32 (and therein the distal portion of lead 22) extends across heart 18. Accordingly, lead 22 may be configured to define a curving distal portion as depicted in FIG. 1A. In some examples, the curving distal portion of lead 22 may help improve the efficacy and/or efficiency of pacing, sensing, and/or defibrillation to heart 18 by IMD 12, in addition to the techniques for controlling the delivery of cardiac therapy described herein.

Electrodes 34A, 34B may be pace/sense electrodes 34A, 34B (individually or collectively, "pace/sense electrode(s) 34") located on the distal portion of lead 22. Electrodes 34 are referred to herein as pace/sense electrodes as they generally are configured for use in delivery of pacing pulses and/or sensing of cardiac electrical signals. In some instances, electrodes 34 may provide only pacing functionality, only sensing functionality, or both pacing functionality and sensing functionality. In the example illustrated in FIG. 1A and FIG. 1B, pace/sense electrodes 34 are separated from one another by defibrillation electrode 32B. In other examples, however, pace/sense electrodes 34 may be both distal of defibrillation electrode 32B or both proximal of defibrillation electrode 32B. In examples in which lead 22 includes more or fewer electrodes 32, 34, such electrodes may be positioned at other locations on lead 22. In some examples, IMD 12 may include one or more electrodes 32, 34 on another lead (not shown). Other lead configurations may be used, such as various electrode arrangements. For example, one or more pace/sense electrodes 34 may be placed between two defibrillation electrodes 32, such as described above. In an example, multiple pace/sense electrodes 34 may be placed between two defibrillation electrodes 32. In an example, two defibrillation electrodes 32 may be adjacent (e.g., such that the two defibrillation electrodes 32 are not separated by any pace/sense electrodes 34 between the two defibrillation electrodes 32). Other arrangements may additionally or alternatively be used.

Lead 22 may define different sizes and shapes as may be appropriate for different purposes (e.g., for different patients or for different therapies). As discussed above, in some examples, the distal portion of lead 22 may have one or more curved sections. As shown in the example of FIG. 1A, the distal portion of lead 22 is a serpentine shape that includes two "C" shaped curves, which together may resemble the Greek letter epsilon, "e." Defibrillation electrodes 32 are each carried by one of the two respective C-shaped portions of the lead body distal portion. The two C-shaped curves extend or curve in the same direction away from a central axis of the lead body. In some examples, pace/sense electrodes 34 may be approximately aligned with the central axis of the straight, proximal portion of lead 22. In such examples, mid-points of defibrillation electrodes 32 are laterally offset from pace/sense electrodes 34. Other examples of extra-cardiovascular leads including one or more defibrillation electrodes and one or more pace/sense electrodes 34 carried by curving, serpentine, undulating or zig-zagging distal portion of lead 22 also may be implemented using the techniques described herein. In some examples, the distal portion of lead 22 may be straight (e.g., straight or nearly straight).

In some examples, the electrode arrangement on lead 22 may correspond to a geometry of lead 22. For example, pace/sense electrodes 34 may be positioned on relative peaks of a curved lead shape, while defibrillation electrodes 32 may be positioned on relative valleys of the curved lead shape. In other examples, the distal portion of lead 22 may include branches, biased portions expanding away from a central shaft, or other shapes (e.g., with one or more of electrodes 32, 34 disposed on the branches, shaft, or biased portions) that may provide appropriate monitoring information or therapy. Deploying lead 22 such that electrodes 32, 34 are thusly at these depicted peaks and valleys of serpentine shape may therein increase an efficacy of system 10. For example, electrodes 32, 34 may have access to better sensing or therapy vectors when lead 22 is deployed into the serpentine shape, in addition to the techniques for controlling the delivery of cardiac therapy described herein.

Orienting the serpentine shaped lead such that pace/sense electrodes 34 are closer to heart 18 may provide better electrical sensing of the cardiac signal and/or lower pacing capture thresholds than if pace/sense electrodes 34 were oriented further from heart 18. The serpentine or other shape of the distal portion of lead 22 may have increased fixation to patient 8 as a result of the shape providing resistance against adjacent tissue when an axial force is applied. Another advantage of a shaped distal portion is that pace/sense electrodes 34 may have access to greater surface area over a shorter length of heart 18 relative to a lead having a straighter distal portion.

In some examples, the elongated lead body of lead 22 may include one or more elongated electrical conductors (not illustrated) that extend within the lead body from the connector at the proximal lead end to electrodes 32, 34 located along the distal portion of lead 22. The one or more elongated electrical conductors contained within the lead body of lead 22 may engage with respective ones of electrodes 32, 34. In one example, each of electrodes 32, 34 is electrically coupled to a respective conductor within lead 22. The respective conductors may electrically couple to circuitry, such as a therapy module or a sensing module, of IMD 12 via connections in connector assembly, including associated feedthroughs. The electrical conductors transmit therapy from a therapy module within IMD 12 to one or more of electrodes 32, 34, and transmit sensed electrical signals from one or more of electrodes 32, 34 to the sensing module within IMD 12.

In some examples, the elongated lead body of lead 22 may have a diameter of between 3 and 9 French (Fr), although lead bodies having diameters less than 3 Fr and more than 9 Fr may also be utilized. In another example, the distal portion and/or other portions of the lead body may have a flat, ribbon or paddle shape. In such examples, the width across the flat portion of the flat, ribbon or paddle shape may be between 1 and 3.5 mm. Other lead body designs may be used without departing from the scope of this disclosure. The lead body of lead 22 may be formed from a non-conductive material, including silicone, polyurethane, fluoropolymers, mixtures thereof, and other appropriate materials, and shaped to form one or more lumens within which the one or more conductors extend. However, the techniques are not limited to such constructions.

In some examples, defibrillation electrodes 32 may have a length greater than 5 centimeters (cm) and less than 10 cm, or a length between about 2 cm to about 16 cm. In other examples, defibrillation electrodes 32 may be a flat ribbon electrode, paddle electrode, braided or woven electrode, mesh electrode, segmented electrode, directional electrode, patch electrode or other type of electrode besides an elongated coil electrode.

Pace/sense electrodes 34 may comprise ring electrodes, short coil electrodes, hemispherical electrodes, segmented electrodes, directional electrodes, or the like. In some examples, pace/sense electrodes 34 may have substantially the same outer diameter as the lead body. In one example, pace/sense electrodes 34 may have surface areas between 1.6-55 mm². Pace/sense electrodes 34 may, in some examples, have relatively the same surface area or different surface areas. Depending on the configuration of lead 22, pace/sense electrodes 34 may be spaced apart by the length of defibrillation electrodes 32, plus some insulated length on each side of defibrillation electrode 32, e.g., approximately 2-16 cm. In other examples, such as when pace/sense electrodes 34 are between segments of a segmented defibrillation electrodes 32, the electrode spacing may be smaller, e.g., less than 2 cm or less than 1 cm. The example dimensions provided above are exemplary in nature and should not be considered limiting of the examples described herein. In other examples, lead 22 may include a single pace/sense electrode 34 or more than two pace/sense electrodes 34.

In some examples, IMD 12 may include one or more housing electrodes (not shown) positioned on housing 20 of IMD 12. Such housing electrodes may be formed integrally with an outer surface of hermetically-sealed housing 20 of IMD 12, or otherwise may be coupled to housing 20. In some examples, a housing electrode may be defined by an uninsulated portion of an outward facing portion of housing 20 of IMD 12. In some examples, housing 20 may define one or more additional housing electrodes, which may be defined by corresponding divisions between insulated and uninsulated portions of housing 20. In still other examples, substantially all of housing 20 may be uninsulated, such that substantially all of housing 20 defines a housing electrode.

In general, system 10 may sense electrical signals, such as via one or more sensing vectors that include combinations of pace/sense electrodes 34 and/or a housing electrode of IMD 12. In some examples, IMD 12 may sense cardiac electrical signals using a sensing vector that includes one or both of the defibrillation electrodes 32 and/or one of defibrillation electrodes 32 and one of pace/sense electrodes 34 or a housing electrode of IMD 12. The sensed electrical intrinsic signals may include electrical signals generated by cardiac muscle and indicative of depolarizations and repolarizations of heart 18 at various times during the cardiac cycle. IMD 12 may be configured to analyze the electrical signals sensed by the one or more sensing vectors to detect tachyarrhythmia, such as ventricular tachycardia (VT) or ventricular fibrillation (VF). In response to detecting the tachyarrhythmia, IMD 12 may begin to charge a storage element, such as a bank of one or more capacitors, and, when charged, delivers substernal electrical stimulation therapy, e.g., ATP, cardioversion or defibrillation shocks, and/or post-shock pacing in response to detecting tachycardia (e.g., VT or VF). In some examples, IMD 12 may generate and deliver bradycardia pacing in addition to ATP, cardioversion or defibrillation shocks, and/or post-shock pacing.

Processing circuitry of IMD 12 may sense patient parameters indicative of a current heart position status of heart 18 based on signals sensed via one or more sensors of system 10. It should be noted that although such processing circuitry may be contained within IMD 12 and/or within another device of system 10 (e.g., external device 38), the processing circuitry is described herein as being a component of IMD 12 for the sake of clarity. In some examples, processing circuitry of system 10 may determine a current posture of patient 8 and/or a respiratory state of patient 8. For example, system 10 may include one or more accelerometers or gyrometers (not shown). The one or more accelerometers may comprise one or more three-axis accelerometers. In some examples, such accelerometers or gyrometers may be a component of IMD 12 of system 10. Signals generated by such sensors may be indicative of, for example, a current posture of patient 8, such as an upright posture, a seated posture, a supine or prone posture, or other postures. In some examples, heart 18 may be positioned up to about 6 cm more caudal, relative to a baseline position, when patient 8 is in an upright posture compared to when patient 8 is in a supine posture.

In some examples, processing circuitry of IMD 12 may determine a respiratory state of patient 8 by determining one or more of an inhalation phase, a respiratory depth, or a respiratory rate of patient 8. In some such examples, processing circuitry of IMD 12 may compare the respiratory depth and/or the respiratory rate to one or more corresponding threshold(s). If the respiratory depth and/or respiratory rate satisfy the corresponding threshold(s), the processing circuitry may, for example, identify the respiratory depth as being "deep" and/or respiratory rate as being "elevated." In some such examples, processing circuitry of IMD 12 may further identify a magnitude of such aspects of patient 8's respiratory state, such as identify the respiratory depth as being "moderately deep" or "very deep." Such magnitudes of the respiratory state may correspond to different position states of heart 18. For example, heart 18 may be positioned more caudal (e.g., up to about 2-4 cm more caudal) during very deep respiration than during moderately deep respiration.

In some examples, processing circuitry of IMD 12 may determine a respiration state of patient 8 based on an impedance between two or more electrodes (e.g., two or more of pace/sense electrodes 34 and/or a housing electrode on housing 20). In other examples, system 10 may include one or more other sensors configured to determine a respiration state of patient 8, such as a microphone configured to detect sounds associated with respiration of patient 8, a magnetometer configured to measure changes in dimensions of anatomical structures of the thorax of patient 8 during respiration, or a pressure sensor configured to measure changes in pressure exerted on lead 22 associated with changes in respiration state. In some examples, an accelerometer may produce a signal that varies based on respiration, e.g., based on vibrations and/or movement associated with respiration. Regardless of the configuration of such sensors, processing circuitry of IMD 12 may determine a posture of patient 8 and/or a respiration state of patient 8 based on the signals obtained therefrom, and associate the posture and/or respiration state of patient 8 with a current heart position state of heart 18 of a plurality of heart position states stored in a memory of system 10 and in association with a respective modification of at least one of a plurality of cardiac sensing, cardiac therapy, or vector parameters.

In some examples, processing circuitry of IMD 12 then may modify at least one cardiac therapy and/or sensing parameter value, according to the modification associated with the current heart position state of heart 18, and control the delivery of the cardiac therapy. For example, processing circuitry of IMD 12 may control delivery of (and IMD may thus deliver) an anti-tachyarrhythmia shock via defibrillation electrodes 32, and or cardiac pacing via pace/sense electrodes 34, according to the modified at least one cardiac therapy parameter value. In some other examples, processing circuitry of IMD 12 may modify an electrode vector, such as a cardiac therapy delivery vector that includes at least two of defibrillation electrodes 32 or a sensing vector that includes at least two of pace/sense electrodes 34, based on the current heart position state of heart 18. In such examples, processing circuitry of IMD 12 may control IMD 12 to at least sense a cardiac electrogram via the modified sensing vector or deliver cardiac therapy via the modified electrode vector.

In some examples, processing circuitry of IMD 12 may modify a cardiac therapy and/or sensing parameter value, according to a modification associated with patient 8's current heart position state in a memory of system 10, by modifying a tachyarrhythmia detection parameter. For example, the tachyarrhythmia detection parameter may be a threshold heart rate (e.g., a certain number of beats per minute over a baseline heart rate) of patient 8. If satisfied, the threshold heart rate may indicate that patient 8 is experiencing tachyarrhythmia. However, patient 8 may have a higher baseline heart rate during inhalation than during exhalation. Thus, processing circuitry of IMD 12 may modify the tachyarrhythmia detection threshold by increasing the tachyarrhythmia detection threshold heart rate when patient 8's heart position state corresponds to an inhalation phase of respiration. In some examples, using an increased tachyarrhythmia detection threshold heart rate during inhalation may improve a tachyarrhythmia-detection accuracy of system 10, such as by reducing a possibility of false-positive tachyarrhythmia detections. In some examples, reducing a possibility of false-positive tachyarrhythmia detections may reduce a possibility of delivering unnecessary anti-tachyarrhythmia shocks to patient 8, which may avoid associated and unnecessary discomfort to patient 8 and/or avoid unnecessary depletion of a power source of system 10.

In some examples, processing circuitry of IMD 12 may modify a cardiac therapy and/or sensing parameter value by which IMD 12 may deliver cardiac therapy, according to a modification associated with patient 8's current heart position state in a memory of system 10, by modifying a cardiac electrogram sensing amplitude threshold. For example, a clinician may select a baseline cardiac electrogram sensing amplitude threshold, when programming IMD 12, that may enable IMD 12 to sense a target portion of a cardiac electrogram via pace/sense electrodes 34 (e.g., an R-wave) for tachyarrhythmia detection when one or more of pace/sense electrodes 34 are positioned approximately over a particular portion of heart 18 such as a ventricle. However, when heart 18 is caudal to a baseline position, such as when patient 8 is in an upright posture and/or inhaling, one or more other portions of the sensed electrogram (e.g., a T-wave) may be more prominent. In some such examples, oversensing of a T-wave or other non-target portions of the electrogram by IMD 12 may result in an increased possibility of a false-positive detection of tachyarrhythmia. Thus, a clinician may program IMD 12 to increase a sensing threshold amplitude associated with such other portions of the cardiac electrogram to reduce a possibility of false-positive tachyarrhythmia detection. For example, processing circuitry of IMD 12 may modify the cardiac electrogram sensing amplitude threshold by increasing a cardiac electrogram sensing amplitude threshold of IMD 12 when a current position of heart 18 is caudal to a baseline position, which may enable system 10 to better sense a target portion of the cardiac electrogram when heart 18 is in such positions.

In some examples, processing circuitry of IMD 12 may modify a cardiac therapy parameter value, according to a modification associated with patient 8's current heart position state in a memory of system 10, by modifying an anti-tachyarrhythmia shock magnitude or an amplitude of one or more pacing pulses by which IMD 12 may deliver cardiac therapy. For example, a clinician may select a baseline anti-tachyarrhythmia shock magnitude or a baseline pacing pulse amplitude (e.g., when programming IMD 12) that may effectively treat a tachyarrhythmia or provide pacing capture of heart 18 when defibrillation electrodes 32 or pace/sense electrodes 34 are positioned approximately over heart 18. However, when heart 18 is caudal to a baseline position, such as when the patient 8 is upright and/or inhaling, one or more of defibrillation electrodes 32 or pace/sense electrodes 34 may no longer be positioned approximately over heart 18. In such cases, an efficacy of an anti-tachyarrhythmia shock delivered by IMD 12 may be reduced or pacing capture may not be maintained during delivery of cardiac pacing pulses by IMD 12. Thus, in such examples, processing circuitry of IMD 12 may modify a cardiac therapy parameter by increasing an anti-tachyarrhythmia shock magnitude or increasing an amplitude of one or more pacing pulses when patient 8's posture and/or respiratory state corresponds to a lower heart position state. In some such examples, increasing an anti-tachyarrhythmia shock magnitude or increasing an amplitude of one or more pacing pulses may improve an efficacy of anti-tachyarrhythmia shock therapy or pacing capture, which may result in an improved clinical outcome of cardiac therapy for patient 8, compared to example cardiac therapy techniques that do not take into account a position of a patient's heart.

In some examples, processing circuitry of IMD 12 may modify a cardiac therapy parameter value, according to a modification associated with a current heart position state of patient 8 in a memory of system 10, by modifying at least one of a sensing vector that includes at least two of pace/sense electrodes 34 or a shock vector that includes at the least two of defibrillation electrodes 32. As discussed above, when heart 18 is caudal to a baseline position, one or more of pace/sense electrodes 34 and/or defibrillation electrodes 32 may no longer be positioned approximately over heart 18. In such examples, processing circuitry of IMD 12 may be configured to modify at least one electrode vector by removing one or more of pace/sense electrodes 34 from the sensing vector or by removing one or more of defibrillation electrodes 32 from the shock vector. The electrodes 34 or 32 removed from the sensing vector or shock vector may be the ones of electrodes 32, 34 no longer positioned over heart 18 when heart 18 is caudal to a baseline position. For example, processing circuitry of IMD 12 may remove from an electrode vector one or more electrodes positioned on a distal portion of the lead, such as one or more most-superior or most-distal ones of electrodes 32 or 34. In some examples, an anti-tachyarrhythmia shock delivered by IMD 12 using such a modified shock vector may improve an efficacy of anti-tachyarrhythmia shock therapy, such as by increasing shock impedance. In some examples, the increased shock impedance of the modified shock vector may more efficiently direct and sustain delivery of energy to heart 18 via the remaining ones of defibrillation electrodes 32 of the modified shock vector, even though IMD 12 may deliver less total energy via the modified shock vector than via a corresponding unmodified shock vector.

In any such examples in which processing circuitry of IMD 12 may modify a cardiac therapy parameter value, according to a modification associated with patient 8's current heart position state in a memory of system 10, the magnitude of the modification may be based on a magnitude of heart movement associated with patient 8's current heart position state. For example, a magnitude of a modification of a cardiac therapy parameter value associated with a first heart position state in which heart 18 is relatively more caudal may be greater than a magnitude of a modification of a cardiac therapy parameter associated with a second heart position state in which heart 18 is caudal to the first heart position state, but still more caudal than a baseline position. In some examples, a difference in positions of heart 18 between such heart positions states may be several centimeters, such as up to about 4 cm.

In some techniques in which processing circuitry of IMD 12 may control IMD 12 to at least sense a cardiac electrogram of patient 8 via a modified vector or deliver cardiac therapy to heart 18 via a modified electrode vector, processing circuitry of IMD 12 may control system 10 to deliver cardiac therapy by controlling IMD 12 to deliver cardiac pacing to heart 18 via the modified vector. As discussed above, when the heart 18 is positioned caudal to a baseline position, such as when patient 8 is upright and/or inhaling, one or more of, pace/sense electrodes 34 may no longer be positioned approximately over a portion of heart 18 to which it may be desirable to deliver pacing pulses, such as a ventricle of heart 18. Instead, one or more of the electrodes may be positioned over an atrium of heart 18 when heart 18 is positioned caudal to a baseline position. Pacing pulses delivered via one or more of pace/sense electrodes 34 positioned over a non-target portion of heart 18 may not contribute to pacing efficacy and may reduce energy efficiency of system 10. Thus, it may be desirable to remove such electrodes 34 from a pacing vector when heart 18 is positioned caudal to a baseline position, which may improve pacing efficiency.

In any of the example techniques described herein, the modifications to the cardiac therapy parameters and/or electrode vectors of system 10 may be selected by a clinician and programmed into a memory of system 10. In some examples, the clinician may select the modifications (e.g., a parameter to modify and/or a magnitude of a modification) based on one or more physiological aspects of patient 8 that may be associated with an amount and/or direction that heart 18 may move with changes in the posture and/or respiration state of patient 8. In some examples, the clinician may directly observe (e.g., via fluoroscopy) an amount and/or direction of movement of heart 18 with changes in the posture and/or respiration state of patient 8. In such examples, processing circuitry of IMD 12 may automatically or semi-automatically modify values of one or more cardiac therapy parameters and/or sensing parameters as heart 18 moves with changes in the posture and/or respiration state of patient 8, which may improve the efficacy and/or efficiency of the cardiac therapy delivered by system 10, such as by more accurately directing energy to target portions of the heart and/or by reducing the delivery of energy to non-target locations.

In some examples, system 10 may include external device 38. External device 38 may be a computing device that is configured for use in a home, ambulatory, clinic, or hospital setting to communicate with IMD 12 via wireless telemetry. Examples of communication techniques used by IMD 12 and external device 38 include radiofrequency (RF) telemetry, which may include an RF link established via Bluetooth, wireless local networks, or medical implant communication service (MICS). The communication may include one-way communication in which one device is configured to transmit communication messages and the other device is configured to receive those messages. Alternatively, or additionally, the communication may include two-way communication in which each device is configured to transmit and receive communication messages.

External device 38 may include communication circuitry configured to communicate with one or more devices of system 10 (e.g., IMD 12) in accordance with the techniques described above. For example, external device 38 may be used to program commands or operating parameters of IMD 12 for controlling functioning of IMD 12 when external device 38 is configured as a programmer for IMD 12. External device 38 may be used to communicate with IMD 12 to retrieve data such as operational data, physiological data accumulated in IMD memory, or the like. As such, external device 38 may function as a programmer for IMD 12, an external monitor for IMD 12, or a consumer device such as a smartphone. External device 38 may be coupled to a remote patient monitoring system, such as CARELINK®, available from Medtronic plc, of Dublin, Ireland. In other examples, a clinician may use external device 38 to program or update therapy parameters that define cardiac therapy, and/or program or update modifications to the cardiac therapy parameters, sensing parameters, and/or electrode vectors associated with the plurality of heart position states, or perform other activities with respect to IMD 12. The clinicians may be a physician, technician, surgeon, electrophysiologist, or other healthcare professional. In some examples, the user may be patient 8.

Although described herein in the context of example IMD 12, the techniques for controlling the delivery of cardiac therapy described herein may be implemented with other types of IMD configured to deliver cardiac therapy. In some examples, the techniques described herein may be implemented with an external defibrillation device, or other devices or systems configured to deliver cardiac therapy. In some examples, system 10 also may include an implantable monitoring device, such as the Reveal LINQ™, commercially available from Medtronic plc.

Figure 2:
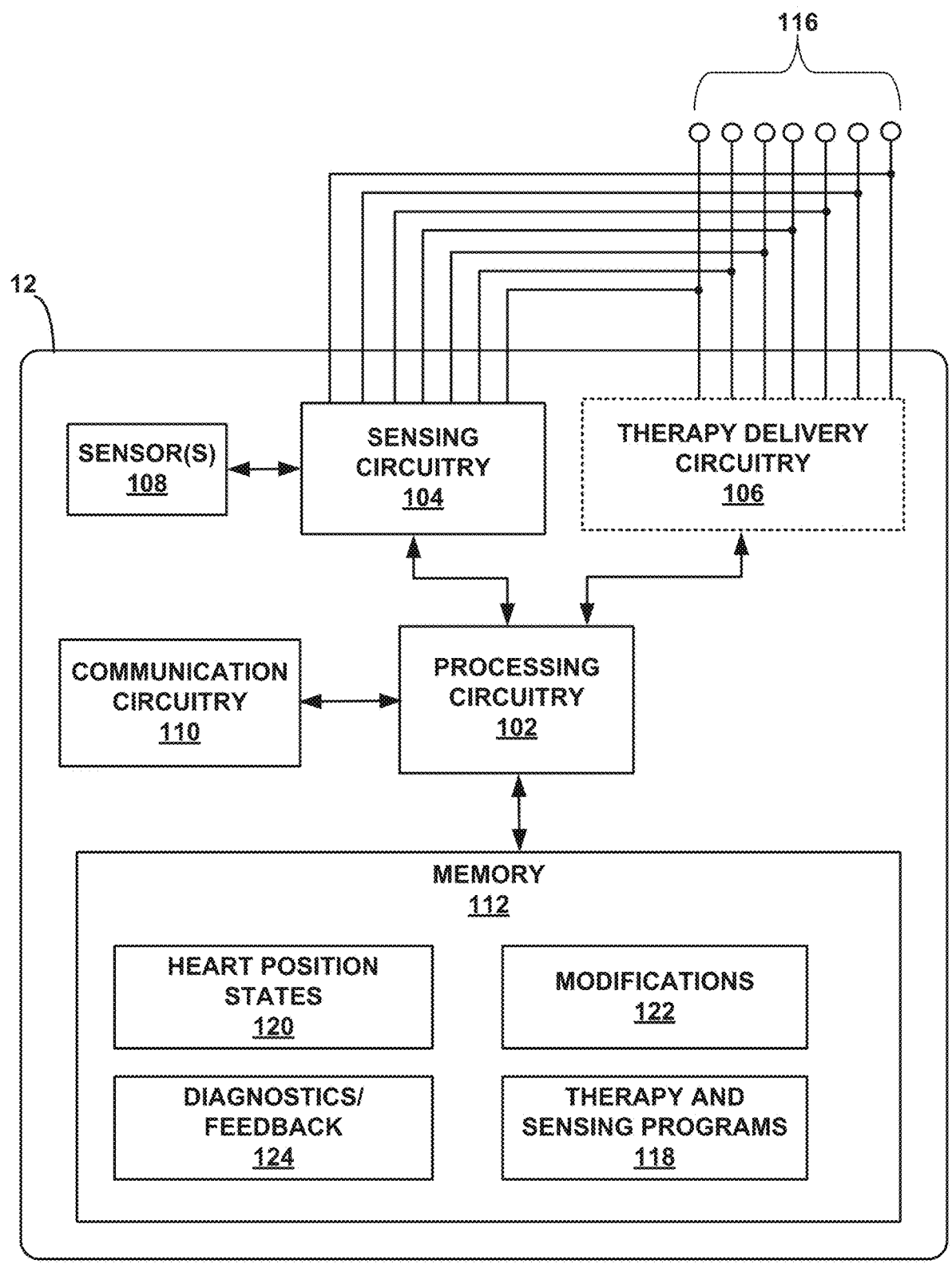
FIG. 2 is a functional block diagram illustrating an example configuration of the example medical device system of FIG. 1A.

FIG. 2 is a functional block diagram illustrating an example configuration of IMD 12 of FIGS. 1A-IC, which may be used to perform any of the techniques described with respect to FIGS. 1A-IC. As shown in FIG. 2, IMD 12 includes processing circuitry 102, sensing circuitry 104, therapy delivery circuitry 106, sensors 108, communication circuitry 110, and memory 112. In addition, IMD 12 includes one or more electrodes 116, which may be any one or more of the previously-described electrodes of IMD 12, one or more of which may be carried by lead 22 or disposed on housing 20 of IMD 12. In some examples, memory 112 includes computer-readable instructions that, when executed by processing circuitry 102, cause IMD 12 and processing circuitry 102 to perform various functions attributed to IMD 12 and processing circuitry 102 herein. Memory 112 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

Processing circuitry 102 may include fixed function circuitry and/or programmable processing circuitry. Processing circuitry 102 may include any one or more of a microprocessor, a controller, a digital signal processor (DSP), an application specific integrated circuit (ASIC), a field-programmable gate array (FPGA), or equivalent discrete or analog logic circuitry. In some examples, processing circuitry 102 may include multiple components, such as any combination of one or more microprocessors, one or more controllers, one or more DSPs, one or more ASICs, or one or more FPGAs, as well as other discrete or integrated logic circuitry. The functions attributed to processing circuitry 102 herein may be embodied as software, firmware, hardware or any combination thereof.

In some examples, processing circuitry 102 may receive (e.g., from external device 38), via communication circuitry 110, a respective value for each of a plurality of cardiac sensing parameters, cardiac therapy parameters (e.g., anti-tachyarrhythmia shock therapy parameters and/or cardiac pacing parameters), and/or electrode vectors. Processing circuitry 102 may store such parameters and/or electrode vectors in therapy and sensing programs 118 of memory 112. Processing circuitry 102 also may receive, in association with each of a plurality of heart position states 120, a respective modification 122 of at least one of the cardiac sensing parameters, cardiac therapy parameters, and/or electrode vectors. Processing circuitry 102 may store the heart position states in heart position states 120 of memory 112, and may store the respective modifications in modifications 122 of memory 112. The modifications may take the form of, as examples, a look-up table or other data structure, or a function.

Processing circuitry 102 may monitor a posture and/or a respiration state of patient 8 via one or more of electrodes 116 and sensors 108. In some examples, processing circuitry 102 may determine a respiration state of patient 8 based on an impedance between two or more of electrodes 116, such as between housing 20 of IMD 12, which may function as a housing electrode, and an electrode positioned on lead 22. Therapy delivery circuitry 106 and/or sensing circuitry 104 may include circuitry to generate a signal, e.g., current or voltage source circuitry, having a known current or voltage amplitude, and switching circuitry to couple the signal to selected ones of electrodes 116. Sensing circuitry 104 may include circuitry to sample the signal and measure the other of voltage or current. Processing circuitry 102 may determine an impedance value associated with the impedance signal based on such measurements. In other examples, processing circuitry 102 may determine a respiration state based on variations in an amplitude of an electrogram (EGM) signal sensed by electrodes 116 that may be associated with movement of heart 18 that may occur with respiration of patient 8.

In some examples, sensors 108 may include one or more gyrometers and/or accelerometers. In some examples, such accelerometers may comprise one or more three-axis accelerometers. Signals generated by such gyrometers and/or accelerometers may be indicative of a current posture of patient 8, such as an upright posture, a seated posture, a supine or prone posture, or other postures. In some examples, an accelerometer may produce a signal that varies based on respiration, e.g., based on vibrations and/or movement associated with respiration. For example, a cyclic component of a signal sensed by an accelerometer may be associated with movement of IMD 12 as the implant site of IMD 12 within patient 8 moves (e.g., tilts) with respiration.

In other examples, sensors 108 may include one or more other sensors configured to determine a respiration state of patient 8, such as a microphone configured to detect sounds associated with respiration of patient 8, a magnetometer configured to sense motion within the earth's magnetic field associated with respiration of patient 8, or a pressure sensor configured to measure changes in pressure exerted on lead 22 associated with changes respiration state.

Sensing circuitry 106 may include filters, amplifiers, and/or analog-to-digital conversion circuitry, as examples, to condition any of these sensed signals for analysis by processing circuitry 102 and/or to detect features of the signals. For example, sensing circuitry 106 may condition an EGM signal to extract variations in an amplitude of the EGM signal that may be associated with movement of heart 18 occurring with respiration of patient 8. In examples in which sensors 108 include a microphone, sensing circuitry 106 may condition an audio signal sensed by a microphone to separate respiratory sounds from interfering background noise. In examples in which sensors 8 include a pressure sensor, sensing circuitry 106 may condition a signal sensed by a pressure sensor to filter out variations caused by atmospheric pressure. In any such examples, processing circuitry 102 may determine a posture of patient 8 and/or a respiration state of patient 8 based on the signals obtained from electrodes 116 and sensors 108, and may associate patient 8's posture and/or respiration state with a current heart position state of heart 18 of the plurality of heart position states 120 stored in heart position states 120 of memory 112.

In some examples, heart position states 120 may be defined by one or more threshold posture and/or respiration values. For example, one or more of heart position states 120 may be defined, at least in part, by a threshold respiration depth value. In such examples, processing circuitry 102 may determine a respiration depth value associated with patient 8's respiration state, such as by determining an impedance between two or more of electrodes 116 and/or analyzing signals sensed by one or more of sensors 108, and determine a current heart position state of heart 18 based, at least in part, on whether the determined respiration depth value satisfies the threshold respiration depth value. In examples in which a heart position state is associated with a posture, the heart position state may be defined, at least in part, by a threshold value associated with the posture. In such examples, the threshold value may be a value (e.g., a voltage) derived from a signal sensed by one or more accelerometers of sensors 108. For example, sensing circuitry 106 may condition a signal sensed by the one or more accelerometers for analysis by processing circuitry 102, such as by applying a low-pass filter to the signal. Processing circuitry 102 then may analyze the conditioned signal to determine a value associated with a current posture of patient 8, and determine a current position state of heart 18 based, at least in part, on whether the determined value satisfies the threshold value associated with the posture.

After determining patient 8's current heart position state as being one of heart position states 120, processing circuitry 102 may modify at least one of a cardiac sensing parameter value, a cardiac therapy parameter value, and/or an electrode vector according to one or more of modifications 122 associated with the current heart position state. Example parameters include a cardiac pacing magnitude (e.g., a pulse amplitude or width), an anti-tachyarrhythmia shock magnitude (e.g., a pulse amplitude, pulse width, and/or shock energy), or cardiac electrogram sensing parameter, such as a threshold amplitude for detecting an R-wave, P-wave, or other feature of the cardiac electrogram. In some examples, the parameter is a tachyarrhythmia detection parameter, which may be a cardiac electrogram sensing parameter used by processing circuitry 102 to detect tachyarrhythmia. In some examples, the parameter is an electrode vector of a plurality of electrodes 116, which processing circuitry 102 may use to sense a cardiac electrogram and/or deliver cardiac therapy via the modified electrode vector. Processing circuitry 102 then may control IMD 12 to deliver cardiac therapy via therapy delivery circuitry 106 according to the modified sensing parameter value, cardiac therapy parameter value, and/or electrode vector. In some other examples, processing circuitry 102 may modify an electrode vector that includes at least two defibrillation electrodes of electrodes 116 or at least two pace/sense electrodes of electrodes 116, based on the current heart position state, and control IMD 12 to at least sense a cardiac electrogram via electrodes 116 and sensing circuitry 104, or deliver cardiac therapy via electrodes 116 and therapy delivery circuitry 106.

In some examples, processing circuitry 102 may modify a cardiac therapy parameter value, according to one or more of modifications 122 associated with patient 8's current heart position state in memory 112, in accordance with the techniques described above with respect to FIGS. 1A-IC. For example, processing circuitry 102 modify a cardiac therapy parameter value, according to a modification 122 associated with patient 8's current heart position state 120, by modifying a tachyarrhythmia detection parameter and/or a cardiac electrogram sensing amplitude threshold stored in therapy and sensing programs 118. In other examples, processing circuitry 102 may modify a cardiac therapy parameter value, according to a modification 122 associated with patient 8's current heart position state 120, by modifying an anti-tachyarrhythmia shock magnitude or an amplitude of one or more pacing pulses stored in therapy and sensing programs 118. In still other examples, processing circuitry 102 may modify a cardiac therapy parameter value, according to a modification associated with patient 8's current heart position state in memory 112, by modifying at least one of a sensing vector that includes at least two pace/sense electrodes of electrodes 116, or a shock vector that includes at least two defibrillation electrodes of electrodes 116.

In some other examples, processing circuitry 102 may control IMD 12 to at least sense a cardiac electrogram of patient 8 via a modified electrode vector or deliver cardiac therapy to heart 18 via a modified electrode vector, in accordance with the techniques described above with respect to FIGS. 1A-IC. For example, processing circuitry 102 may modify a vector including at least two of electrodes 116, according to a modification 122 associated with patient 8's current heart position state 120, by modifying an electrode vector stored in therapy and sensing programs 118.

In any such examples, processing circuitry 102 also may control IMD 12 to sense a cardiac electrogram or deliver cardiac therapy (e.g., anti-tachyarrhythmia shock or cardiac pacing), via electrodes 116 and sensing circuitry 104 or therapy delivery circuitry 106, based on one or more of the modified sensing parameter value, cardiac therapy parameter value, or modified electrode vector. Processing circuitry 102 thus may improve the efficacy and/or efficiency of the cardiac therapy delivered by system 10, such as by more accurately directing energy to target portions of the heart and/or by reducing the delivery of energy to non-target locations.

A clinician may enter, or processing circuitry 102 may itself determine and recommend, one or more of therapy and sensing programs 118, heart position states 120, or modifications 122 into memory 112, such as via external device 38 or a remote computer, based on one or more factors such as a gender, age, size, or observed heart motion of patient 8. The factors may be provided to processing circuitry 102 by the clinician, e.g., via external device 38. In some examples, the clinician and/or processing circuitry 102 may update one or more of therapy and sensing programs 118, heart position states 120, or modifications 122 periodically or on an as-needed basis. For example, the clinician or processing 102 circuitry may determine that a magnitude of one or more of modifications 122 has not effectively countered a reduction in cardiac therapy efficacy or efficiency associated with a particular one of heart position states 120, such as based on data stored in diagnostics/feedback 124 of memory 112. In some such examples, the clinician may enter one or more updated values of modifications 122 into external device 38 or a remote computer, or processing circuitry 102 may recommend updated values via external device 38. Processing circuitry 102 then may receive the updated modifications 122 (or, in other examples, updated therapy and sensing programs 118 and/or heart positions 120) from the external device 38 or the remote computer, and may store such updated values in memory 112.

Diagnostics/feedback 124 of memory 112 may include data pertaining to one or more of determined heart position states of patient 8, determined postures and/or respiration states of patient 8, or the efficacy or efficiency of cardiac therapy delivered by IMD 12. For example, diagnostics/feedback 124 may store efficacy determinations made by processing circuitry 102 based on whether cardiac therapy delivered by IMD 12 according to one or more modified cardiac therapy parameter values and in association with one of heart position states 120 was successful in terminating a tachyarrhythmia or maintaining pacing capture. Diagnostics/feedback 124 also may store efficiency determinations made by processing circuitry 102 based on data pertaining to, e.g., an amount of energy delivered to treat a tachyarrhythmia or maintain pacing capture when processing circuitry 102 controls IMD 12 to deliver cardiac pacing according to one or more cardiac therapy parameter values and in association with one of the heart position states 120. In some examples, a clinician may review such efficacy and/or efficiency determinations stored in diagnostics/feedback 124, and use such data in determining whether to update one or more of therapy and sensing programs 118, heart positions 120, or modifications 122. In some examples, diagnostics/feedback 124 may store system diagnostics pertaining to the functioning of IMD 12 or other components of a medical device system including IMD 12.

Therapy and sensing programs 118 may include values of one or more therapy and sensing parameters. In some examples, ones of therapy and sensing programs 118 may correspond to a type of cardiac therapy, such as anti-tachyarrhythmia shock therapy or cardiac pacing therapy. For example, one of therapy and sensing programs 118 may include values of one or more sensing parameters and one or more therapy parameters that may be appropriate for the sensing a heart rate of patient 8 during cardiac pacing therapy and delivering cardiac pacing therapy to heart 18, such as a sensing amplitude threshold, a pacing pulse amplitude or width, sensing or pacing electrode vectors, or pulse delivery timing. Another one of therapy and sensing programs 118 may include values of one or more sensing parameters and one or more therapy parameters that may be appropriate for sensing a heart rate of patient 8 during tachyarrhythmia detection, and delivering anti-tachyarrhythmia therapy to heart 18, such as a tachyarrhythmia sensing amplitude threshold, an anti-tachyarrhythmia shock magnitude, tachyarrhythmia sensing electrode vectors or defibrillation electrode vectors, or anti-tachyarrhythmia shock delivery timing.

Sensing circuitry 104 and therapy delivery circuitry 106 may be selectively coupled to electrodes 116, e.g., via switching circuitry (not shown) as controlled by processing circuitry 102. The switching circuitry may include one or more transistors or other circuitry for selectively coupling electrodes 116 to other circuitry of IMD 12. Sensing circuitry 104 may monitor signals from electrodes 116 in order to monitor electrical activity of heart (e.g., to detect depolarizations for heart rate determination and/or to produce a cardiac electrogram for morphological or other analyses). Sensing circuitry 104 (or therapy delivery circuitry 106 may also generate a signal via electrodes 116, from which sensing circuitry 104 may produce a thoracic impedance signal, from which sensing circuitry 104 and/or processing circuitry 102 may sense respiration, e.g., magnitude and/or rate. Sensing circuitry 104 may also monitor signals from one or more other sensor(s) 108, such as the one or more accelerometers, gyrometers, magnetometers, barometers, or other sensors configured to determine a posture and/or respiration state of patient 8. Sensing circuitry 104 may monitor signals from any electrodes or other sensors that may be positioned on IMD 12 or on another device in communication with IMD 12. In some examples, sensing circuitry 104 may include one or more filters and amplifiers for filtering and amplifying signals received from one or more of electrodes 116 and/or the one or more sensor(s) 108. Sensing circuitry 104 may also include rectification circuitry, sample-and-hold circuitry, one or more comparators, and/or analog-to-digital conversion circuitry. The functionality provided by such circuitry may be applied to the signal in the analog or digital domain.

Therapy delivery circuitry 106 may include circuitry for generating a signal, such as one or more capacitors, charge pumps, and/or current sources, as well as circuitry for selectively coupling the signal to electrodes 116, e.g., transistors or other switching circuitry.

Communication circuitry 110 may include any suitable hardware, firmware, software or any combination thereof for communicating with another device, such as external device 38, or another IMD or sensor, such as a pressure sensing device. For example, communication circuitry 110 may include voltage regulators, current generators, oscillators, or circuitry for generating a signal, resistors, capacitors, inductors, and other filtering circuitry for processing received signal, as well as circuitry for modulating and/or demodulating a signal according to a communication protocol. Communication circuitry 110 may also include transistors or other switching circuitry for selectively coupling transmitted signal to or receiving signals from an antenna of IMD 12 (not shown) or electrodes 116 (e.g., in the case of tissue conductance communication (TCC)). Under the control of processing circuitry 102, communication circuitry 110 may receive downlink telemetry from, as well as send uplink telemetry to, external device 38 or another device. In some examples, communication circuitry 110 may communicate with external device 38. In addition, communication circuitry 110 may communicate with a networked computing device via an external device (e.g., external device 38) and a computer network, such as the Medtronic CareLink® Network developed by Medtronic, plc, of Dublin, Ireland, as further described below with respect to FIG. 3.

A clinician or another user may retrieve data from IMD 12 using external device 38, or by using another local or networked computing device (e.g., a remote computer located with the clinician) configured to communicate with processing circuitry 102 via communication circuitry 110. In some examples, the clinician may also program parameters of IMD 12 using external device 38 or another local or networked computing device. For example, the clinician may update heart position states 120, modifications 122, and/or values associated with therapy and sensing programs 118.

Although processing circuitry 102 of IMD 12 is described above as being configured to receive signals from sensors 108, determine a current heart position status of patient 8, modify at least one cardiac therapy parameter value, cardiac sensing parameter value, and/or electrode vector according to modifications 122 associated with the current heart position state and control IMD 12 to deliver cardiac therapy and/or sense a cardiac electrogram according to the modified at least one cardiac therapy parameter value, modified cardiac sensing parameter value or modified electrode vector, and carry out other steps of the techniques described herein, any steps described herein as being carried out by processing circuitry 102 of IMD 12 may be carried out by processing circuitry of one or more other devices. For example, processing circuitry of external device 38, a remote computer, or any other suitable implantable or external device or server, may be configured to carry out one or more of the steps of the techniques described herein, such as via communication circuitry 110 of IMD 12.

Figure 3:
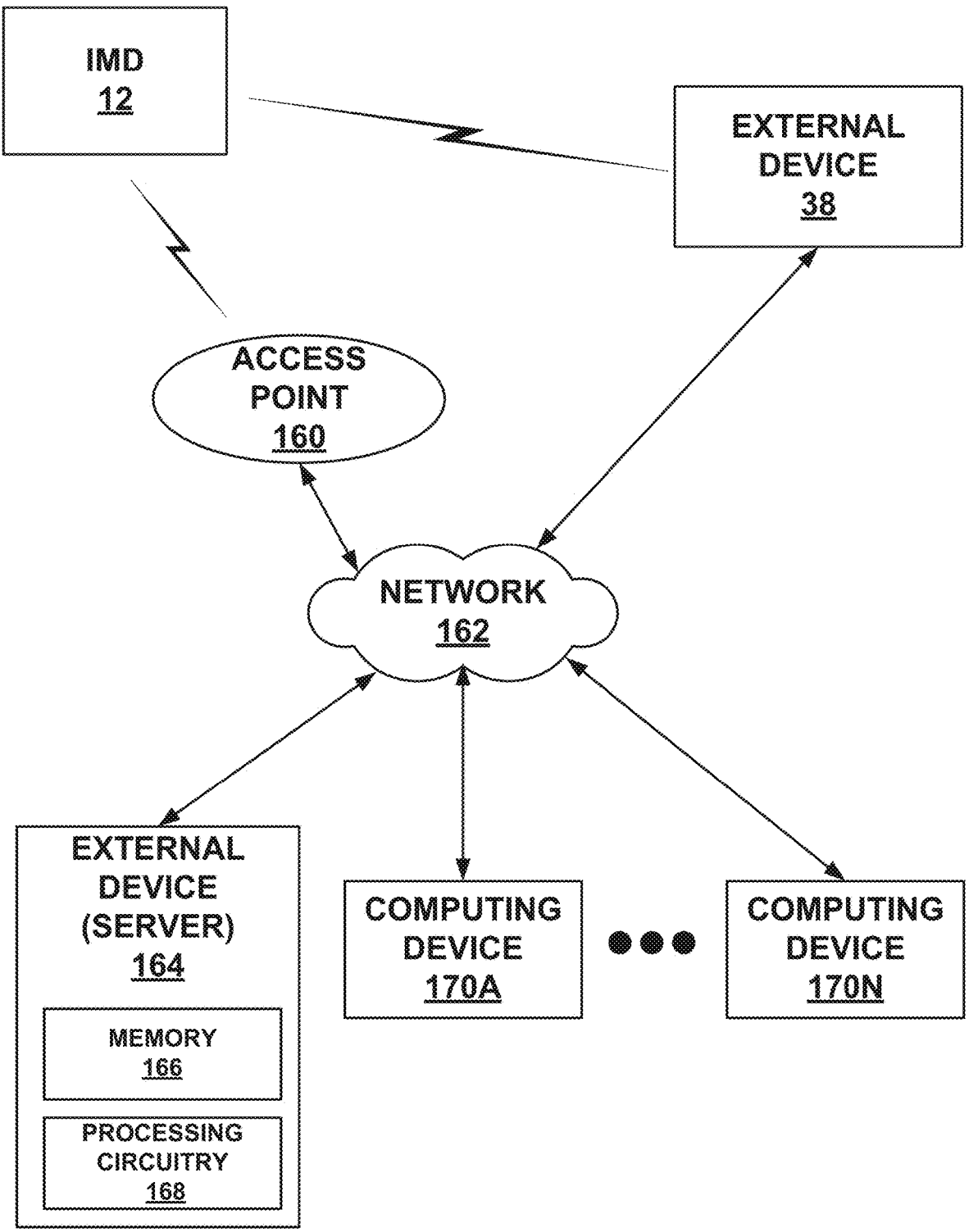
FIG. 3 is a functional block diagram illustrating an example system that includes an external device, such as a server, and one or more computing devices that are coupled to an implantable medical device and the external device of FIG. 1A via a network.

FIG. 3 is a functional block diagram illustrating an example system that includes an access point 160, a network 162, external computing devices, such as a server 164, and one or more other computing devices 170A-170N, which may be coupled to IMD 12 of FIG. 2 and external device 38 via network 162. In this example, IMD 12 may use communication circuitry 110 to communicate with external device 38 via a first wireless connection, and to communicate with an access point 160 via a second wireless connection. In the example of FIG. 3, access point 160, external device 38, server 164, and computing devices 170A-170N are interconnected and may communicate with each other through network 162.

Access point 160 may comprise a device that connects to network 162 via any of a variety of connections, such as telephone dial-up, digital subscriber line (DSL), or cable modem, or other suitable connections. In other examples, access point 160 may be coupled to network 162 through different forms of connections, including wired or wireless connections. In some examples, access point 160 may be a user device, such as a tablet or smartphone, that may be co-located with the patient. In some examples, IMD 12 may be configured to transmit data, such as cardiac therapy delivery efficacy and/or efficiency data stored in diagnostics/feedback 124 of memory 112, to external device 38. In addition, access point 160 may interrogate IMD 12, such as periodically or in response to a command from patient 8, a clinician, or network 162, in order to retrieve therapy and sensing programs 118, heart position states 120, modifications 122, diagnostics/feedback 124, or other information stored in memory 112 of IMD 12. Access point 160 may then communicate the retrieved data to server 164 via network 162.

In some cases, server 164 may be configured to provide a secure storage site for data collected from IMD 12 and/or external device 38. In some cases, server 164 may assemble data in web pages or other documents for viewing by trained professionals, such as clinicians, via computing devices 170A-170N. One or more aspects of the illustrated system of FIG. 3 may be implemented with general network technology and functionality, which may include or be similar to that provided by the Medtronic CareLink® Network developed by Medtronic plc, of Dublin, Ireland. In some examples, the network technology and functionality may validate a communication transmitted from device, such as a device purporting to be one or more of computing devices 170A-170N (e.g., a purported remoter computer located with a clinician) toward IMD 12. In some examples, such security features may protect the cardiac therapy delivered by IMD 12 to patient 8 from being disrupted, hacked, or otherwise altered by communications originating from unauthorized sources.

In some examples, one or more of computing devices 170A-170N (e.g., device 170A) may be a remote computer, such as a smartphone, tablet or other smart device located with a clinician, by which the clinician may program, receive alerts from, and/or interrogate IMD 12. For example, the clinician may access patient requests, symptoms, undesired effects, and/or efficacy indications through device 170A, such as when patient 8 is in between clinician visits, such as to check on one or more aspects of cardiac therapy delivered by IMD 12, as desired. In some examples, the clinician may enter medical instructions for patient 8 into an application in device 170A, such as an instruction for patient 8 to schedule a visit with the clinician or for patient 8 to seek other medical attention, based on data retrieved from IMD 12 by device 170A, or based on other patient data known to the clinician. Device 170A then may transmit the instructions for medical intervention to a receiving device located with patient 8.

Figure 4:
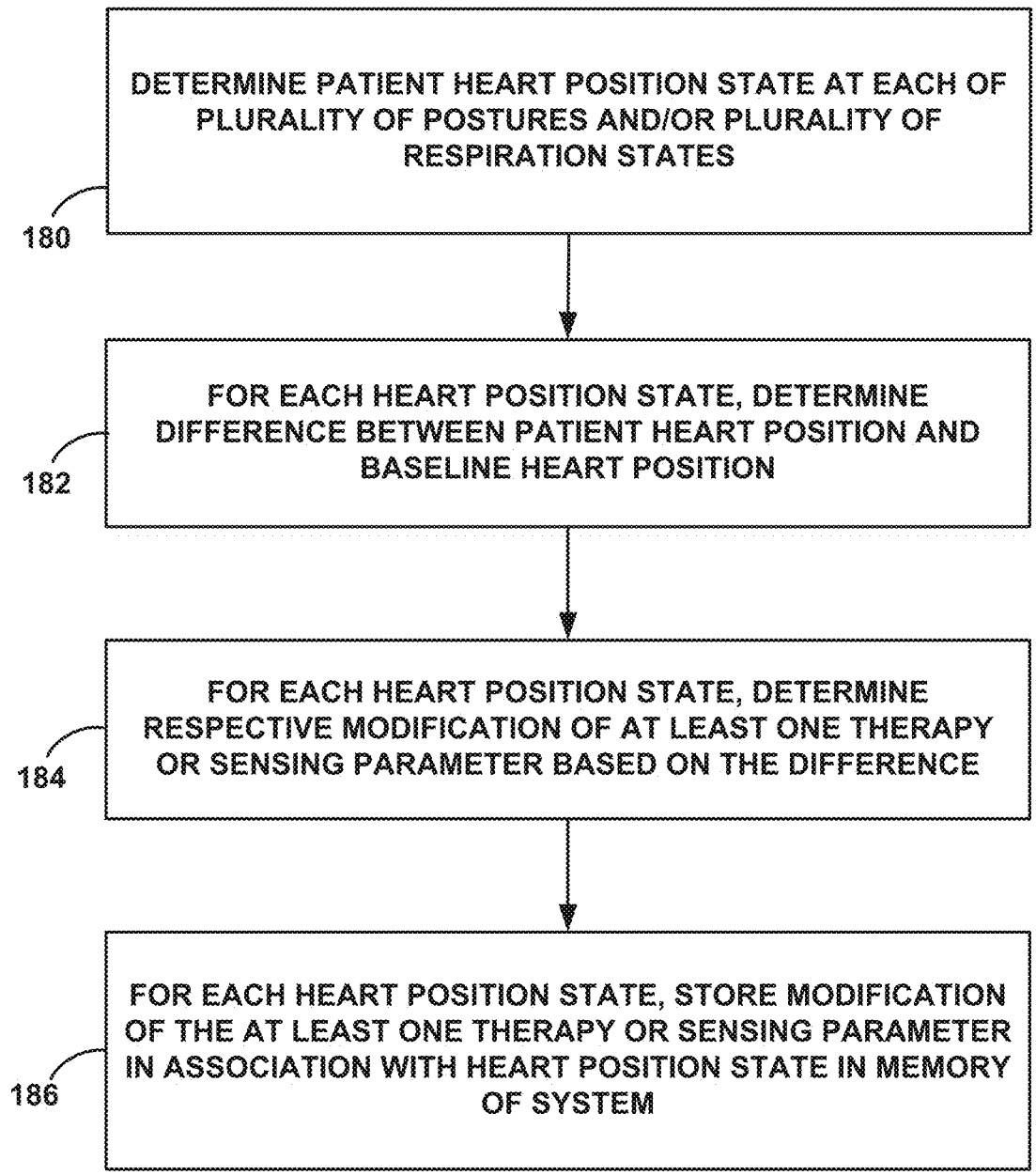
FIG. 4 is a flow diagram illustrating an example technique for determining, in association with each of a plurality of heart position states, a respective modification of at least one therapy parameter.
Figure 5:
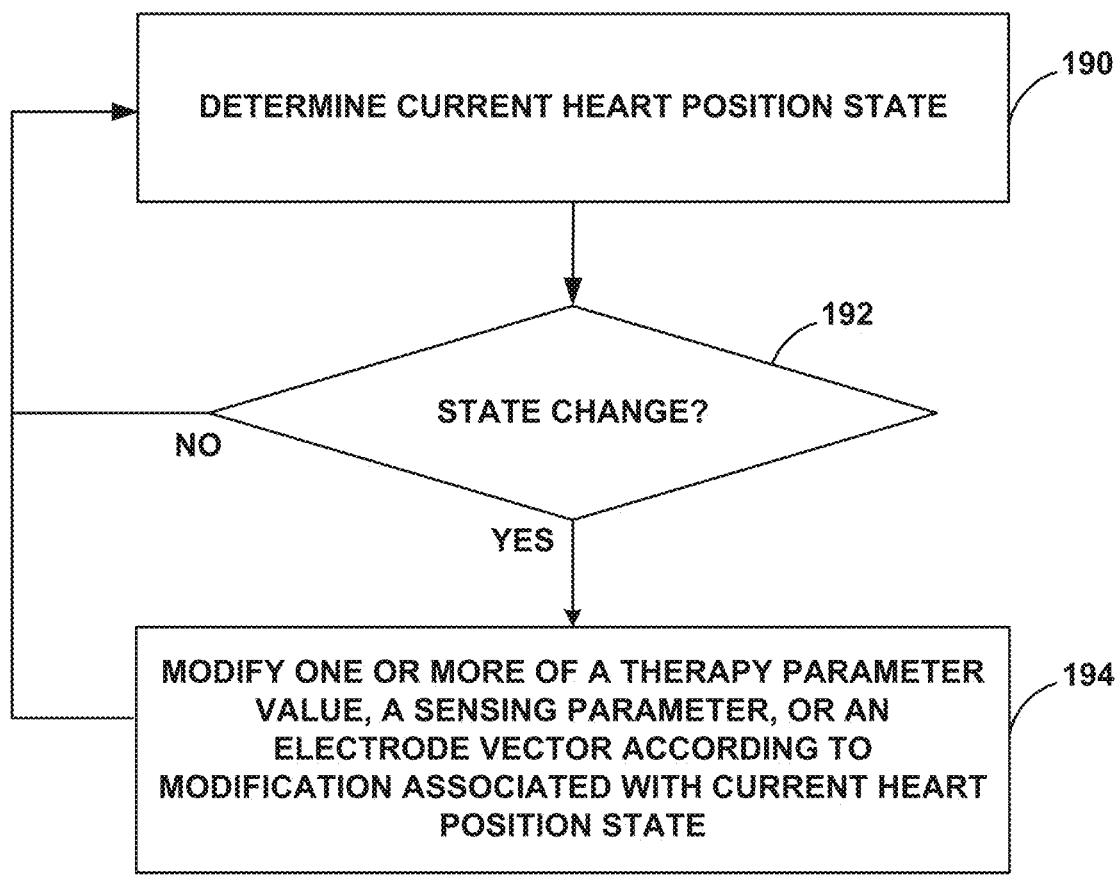
FIG. 5 is a flow diagram illustrating an example technique for modifying at least one therapy parameter value according to a modification associated with a current heart position state of the patient based on determining that a heart position state of the patient has changed.
Figure 6:
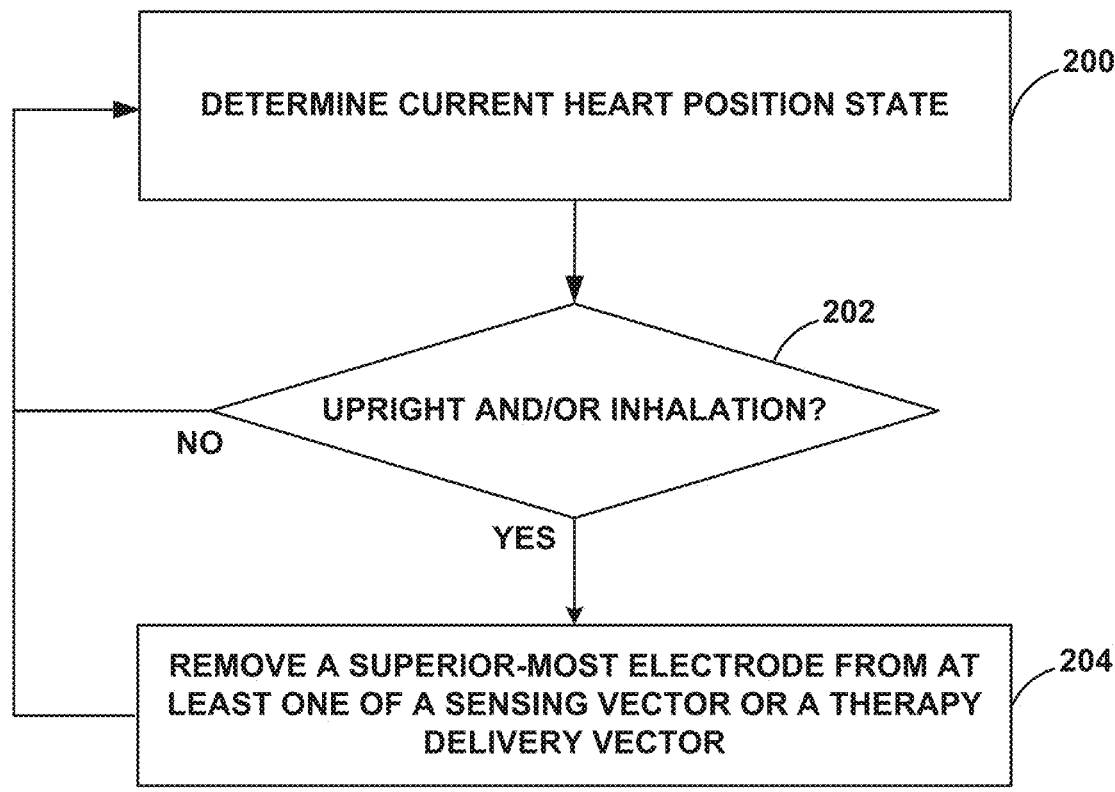
FIG. 6 is a flow diagram illustrating an example technique for modifying an electrode vector based on determining that a heart position state of the patient has changed.

FIGS. 4-6 are flow diagrams illustrating various example techniques related to controlling the delivery of cardiac pacing by IMD 12 to heart 18 according to a requested value of a therapy parameter, in accordance with examples of this disclosure. As described herein, the example techniques illustrated in FIGS. 4-6 may be employed using IMD 12 and an external device (e.g., external device 38 of FIG. 1A), in conjunction with patient 8 as described above with respect to FIGS. 2 and 3. Although described as being performed by IMD 12, the techniques of FIGS. 4-6 may be performed, in whole or in part, by processing circuitry and memory of other devices of a medical device system, as described herein. For example, although processing circuitry 102 of IMD 12 is described as carrying out most of the example techniques illustrated in FIGS. 4-6 for the sake of clarity, in other examples, one or more devices (e.g., a remote computer located with a clinician or other external device or server) may carry out one or more steps attributed herein to processing circuitry 102 of IMD 12.

FIG. 4 is a flow diagram illustrating an example technique for determining, in association with each of a plurality of heart position states, a respective modification of at least one therapy or sensing parameter. In the example technique of FIG. 4, processing circuitry 102 may determine a heart position state of patient 8 for each of a plurality of postures and/or for each of a plurality of respiration states (180), such as by receiving, from external device 38 or another external device, one or more indications by a user of postures and/or respiratory states of patient 8 for which system 10 should modify therapy and/or sensing parameters.

For each of the plurality of heart position states, processing circuitry 102 then determines a difference between the heart position state and baseline heart position state (182). In some examples, the baseline heart position state may be a position of heart 18 when patient 8 is supine and not breathing deeply, rapidly, or inhaling. Each heart position state of the plurality of heart position states may differ from the baseline heart position state by a magnitude of a distance between a portion of heart 18 (e.g., an apex) in the baseline state and the portion of the heart in the heart position state. In some examples, processing circuitry 102 may determine the distance as being a distance in a single plane (e.g., a transverse plane), or as being a distance in more than one plane (e.g., a transverse plane and a frontal plane).

Next, for each heart position state of the plurality of heart position states, processing circuitry 102 determines one or more respective modifications of one or more of a sensing parameter, a therapy delivery parameter, and/or an electrode vector based on the difference between the heart position state and the baseline heart position (184). In some examples, a magnitude of a modification of a cardiac therapy parameter determined by processing circuitry 102 may correspond to the magnitude of the difference between the heart position state and the baseline heart position. For example, heart position states in which heart 18 is relatively further from the baseline heart positions may be associated with a modification of a cardiac therapy parameter that is greater than a modification of the same cardiac therapy parameter associated with a heart position state that is relatively closer to the baseline heart position.

Next, for each heart position state of the plurality of heart position states, processing circuitry 102 stores the determined one or more respective modifications of the one or more therapy or sensing in a memory of system 10, such as in modifications 122 of memory 112 of IMD 12 (186). In some examples, processing circuitry 102 may store such modifications in memory 112 in association with a particular heart position state. For example, processing circuitry 102 may store a modification of tachyarrhythmia detection parameter and an anti-tachyarrhythmia shock magnitude in association with a particular heart position state, such as a heart position state in which heart 18 is caudal to a baseline position. In other examples, processing circuitry may store a single modification of one or more of therapy or sensing parameters in memory 112 in association with a heart position state.

FIG. 5 is a flow diagram illustrating an example technique for modifying at least one therapy or sensing parameter value according to a modification associated with a current heart position state of heart 18 based on determining that a heart position state of heart 18 has changed. In the example technique of FIG. 5, processing circuitry 102 may determine a current position state of heart 18 of patient 8 (190). For example, as discussed above with respect to FIGS. 1A-2, processing circuitry 102 may determine a current position state of heart 18 based on one or more of a current posture or a current respiration state of patient 8, which processing circuitry 102 may determine based on signals received from electrodes of system 10 (e.g., pace/sense electrode 34 or sensing electrodes of electrodes 116) or from one or more sensors 108, such as in the manner described above with respect to FIG. 2.

Next, processing circuitry 102 determines whether the heart position state of heart 18 has changed (192). In some examples, processing circuitry 102 may determine whether the heart position state of heart 18 has changed relative to the baseline heart position state described above (e.g., with respect to FIG. 4). In other examples, processing circuitry 102 may determine whether the heart position state of heart 18 has changed relative to a previously-determined heart position state of heart 18 determined by processing circuitry 102, such as a last-determined heart position state. In either example, if processing circuitry 102 determines that the heart position state of heart 18 has changed ("YES" at 192), then processing circuitry 102 modifies one or more of a cardiac therapy parameter value, a sensing parameter, or an electrode vector according to the modification 122 associated with the current heart position state of heart 18 in memory 112 (194).

If processing circuitry 102 determines that the heart position state of heart 18 has not changed ("NO" at 192), then processing circuitry 102 returns to (190), and again determines a current heart position state of heart 18 (e.g., an updated current heart position state of heart 18) (194). In some examples, processing circuitry 102 may determine a current heart position state of heart 18 multiple times per respiratory cycle of patient 8. For example, processing circuitry 102 may determine a current heart position of heart 18 during an inhalation phase and during an exhalation phase of a respiratory cycle. In other examples, processing circuitry 102 may determine a current heart position of heart 18 according to a different timing schedule, such as during a predetermined length of time at predetermined intervals. In some examples, processing circuitry 102 may determine a respiratory state of patient 8 more frequently than a posture of patient 8. For example, a heart position state of heart 18 may change more frequently due to a respiration state of patient 8 than due to a posture state of patient 8. In such examples, processing circuitry 102 may determine a heart position state of heart 18 each time processing circuitry 102 determines a current respiratory state of patient 8, regardless of whether processing circuitry 102 has substantially concurrently determined a new posture state of patient 8. In any such examples, a clinician may program intervals at which processing circuitry 102 may determine one or more of a posture, respiration state, or heart position state into memory 112 when the clinician programs other data into memory 112 (e.g., as described above with respect to FIG. 2).

FIG. 6 is a flow diagram illustrating an example technique for modifying an electrode vector based on determining that a heart position state of heart 18 has changed. In the example technique of FIG. 6, processing circuitry 102 may determine a current position state of heart 18 of patient 8 (200), such as described above with respect to FIG. 5. Next, processing circuitry 102 determines whether the heart position state of heart 18 corresponds to one or more of an upright posture, inhalation, deep breathing, or any other posture and/or respiration state associated with heart 18 being positioned relatively low in the thorax of patient 8 (202). If processing circuitry 102 determines that the heart position state of heart 18 corresponds to one or more of an upright posture, inhalation, deep breathing, or any other posture and/or respiration state associated with heart 18 being positioned relatively low in the thorax of patient 8 ("YES" at 202), then processing circuitry 102 modifies an electrode vector (e.g., a sensing vector, a pacing vector, or an anti-tachyarrhythmia vector) according to the modification 122 associated with the current heart position state of heart 18 in memory 112 (204).

If processing circuitry 102 determines that the heart position state of heart 18 does not correspond to one or more of an upright posture, inhalation, deep breathing, or any other posture and/or respiration state associated with heart 18 being positioned relatively low in the thorax of patient 8 ("NO" at 202), then processing circuitry 102 returns to (200) and again determines a current heart position state of heart 18 (e.g., an updated current heart position state of heart 18), such as in the manner described above with respect to FIG. 5. In this manner, processing circuitry 102 may enable system 10 to more accurately sense one or more aspects of a cardiac electrical signal and/or deliver more efficacious and/or more efficient cardiac therapy to heart 18. In any such examples, improving sensing accuracy or efficacy and/or efficiency of cardiac therapy delivery advantageously may result in one or more of an improved clinical outcome of patient 8 or an improved longevity of a power source of system 10.

Although processing circuitry 102 of IMD 12 is described above as being configured to perform one or more of the steps of the techniques described with respect to FIGS. 1-6, any steps of the techniques described herein may be performed by processing circuitry of the other devices. For example, processing circuitry of a remote computer located with a clinician (e.g., computing device 170A), or of any other suitable implantable or external device or server, may be configured to perform one or more of the steps described as being performed by processing circuitry 102 of IMD 12. Such other implantable or external devices may include, for example, an implantable or external monitoring device, or any other suitable device.

Various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, electrical stimulators, or other devices. The term "processor" or "processing circuitry" may generally refer to any of the foregoing logic circuitry, alone or in combination with other logic circuitry or any other equivalent circuitry.

In one or more examples, the functions described in this disclosure may be implemented in hardware, software, firmware, or any combination thereof. If implemented in software, the functions may be stored on, as one or more instructions or code, a computer-readable medium and executed by a hardware-based processing unit. Computer-readable media may include computer-readable storage media forming a tangible, non-transitory medium. Instructions may be executed by one or more processors, such as one or more DSPs, ASICs, FPGAs, general purpose microprocessors, or other equivalent integrated or discrete logic circuitry. Accordingly, the terms "processor" or "processing circuitry" as used herein may refer to one or more of any of the foregoing structures or any other structure suitable for implementation of the techniques described herein.

In addition, in some aspects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements. The techniques of this disclosure may be implemented in a wide variety of devices or apparatuses, including an IMD, an external programmer, a combination of an IMD and external programmer, an integrated circuit (IC) or a set of ICs, and/or discrete electrical circuitry, residing in an IMD and/or external programmer.

Experimental Results

This disclosure includes the following discussion which forms part of this disclosure. The following discussion may provide many details and examples consistent with this disclosure. As described further below, one or more studies and experiments were carried out to evaluate one or more aspects of examples of the disclosure. However, the disclosure is not limited by the studies and experiments.

For example, the details and examples of the following discussion may quantify variation of cardiac signal sensing by an EV-ICD based on respiration and posture. The modeling in such examples may similarly be used quantify variation in pacing and or anti-tachyarrhythmia shock parameters desired in response to varying posture and respiration states to achieve therapeutic benefit with efficient use of power resources. The examples of the following may also further illustrate movement of the heart with changing posture and respiration state, as well as the effect of such movement on the position of the heart relative to the electrical field generated using more superior/distal electrode(s) for pacing and/or shock therapy.

In some examples, an EV ICD uses a defibrillation lead placed outside the heart in the anterior mediastinal space. In that location, the electrodes may have some freedom of movement relative to the heart with changing posture. The degree of influence of this motion on electrograms acquired via electrodes in this novel implant location have not been systematically characterized. Studies were carried out to quantify the variation in sensed signals due to changes in posture and respiration.

A first modeling study used sets of MRI scans acquired in various postures and respiratory states to derive anthropometric data quantifying organ motion and shape relative to a supine, end inhalation posture representative of the implant condition. Detailed data for critical anatomy, such as the heart and epicardial fat, was obtained from high resolution ex vivo MRI scans and fused with the lower resolution MRIs to create anatomies with appropriate levels of detail for accurate simulation. Matched sets of computational meshes were created, representing a subject in various poses, and then the ICD is "implanted" multiple times in matched positions across these postures. Epicardial potentials were separately estimated from body surface recordings and mapped onto the myocardial surface.

Figure 7:
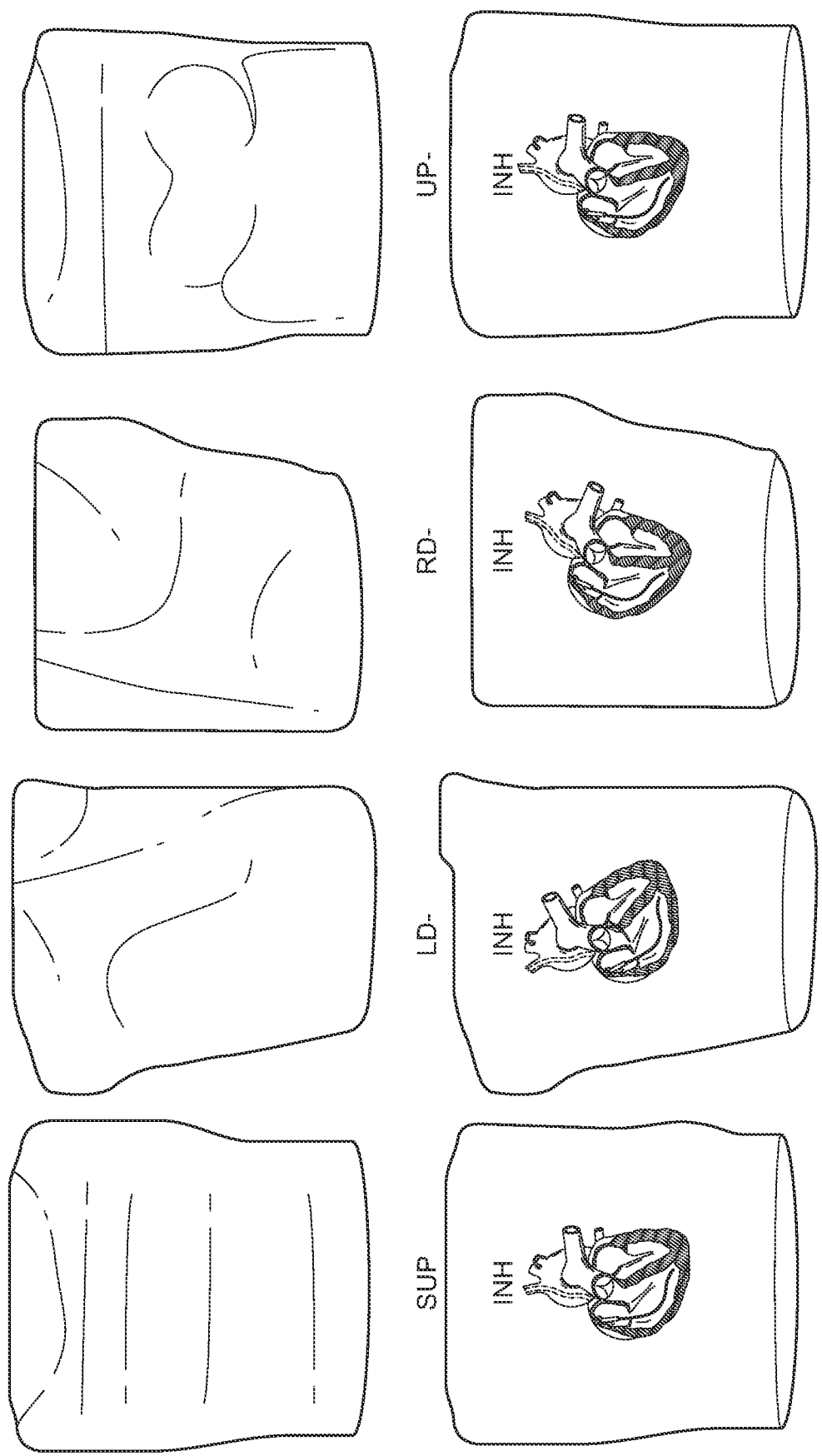
FIG. 7 is a diagram illustrating four MRI scans (top) and corresponding models (bottom) showing the location of a patient's heart within the patient.

FIG. 7 is a diagram illustrating four MRI scans (top) and corresponding models (bottom) showing the location of a patient's heart within the patient (e.g., within the thoracic cavity) at inhalation (INH) of the patient in a supine (SUP), lying down on left side (LD), lying down on right side (RD), and upright (UP) posture. As shown, the relative position of the patient's heart was different for each the different postures. In one patient. 20 mm cranial/caudal movement of the heart was observed during tidal breathing and 60 mm of movement was observed during deep breathing.

The epicardial potential data was manually annotated with scoring windows identifying various types of beats such as normal sinus rhythm (NSR) or ventricular tachycardia (VT). An automated system computed the cardiac signals at the ICD's electrodes for more than 2000 datasets, scored them automatically and stored these results in a database for statistical analysis.

Figure 8:
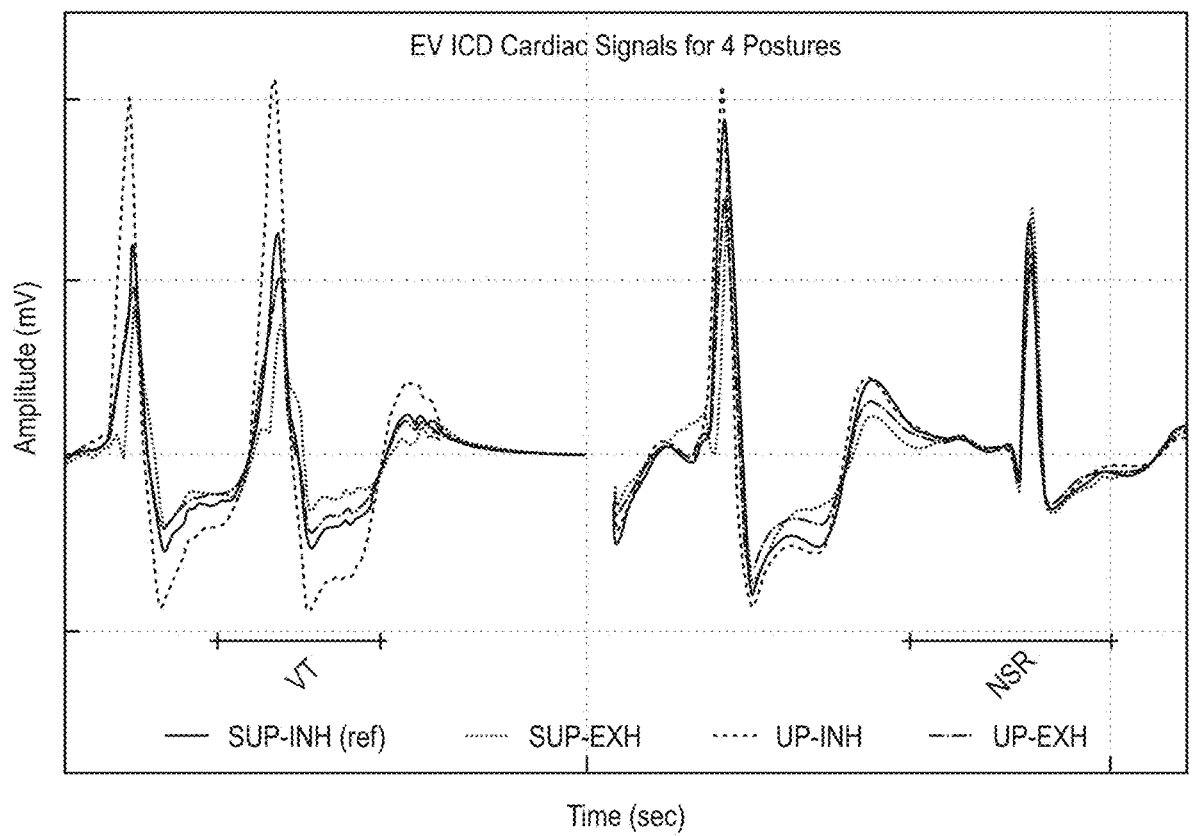
FIG. 8 is a plot of EV ICD cardiac signals for four postures of a patient.

From the motion analysis of the MRI image data it was found that the average cranial-caudal motion of the heart apex was 34 mm (range: 3 to 70 mm, N=9). An example of the predicted signal, with scoring windows, is shown in the FIG. 8 for four combinations of the supine (SUP), upright (UP), inhalation (INH) and exhalation (EXH) denoted by SUP-INH, SUP-EXH, UP-INH and UP-EXH. In this single example, the baseline to peak amplitude, in millivolts (mVpk) for an NSR complex ranges from 1.46 to 2.09 mVpk while a VT complex ranges from 0.75 to 2.22 mVpk. For both complexes the minimum amplitude is associated with the supine, exhalation posture (SUP-EXH) and the maximum amplitude is for the upright, inhalation posture (UP-INH).

Results from the modelling were useful to assess both signal amplitude and postural stability. The results were also used to test guidelines for device and lead implant locations to assure adequate signal levels in all postures for successful arrhythmia detection. The inclusion of postural variation is essential for assuring ambulatory performance of an EV ICD with electrodes outside the heart.

Figure 9B:
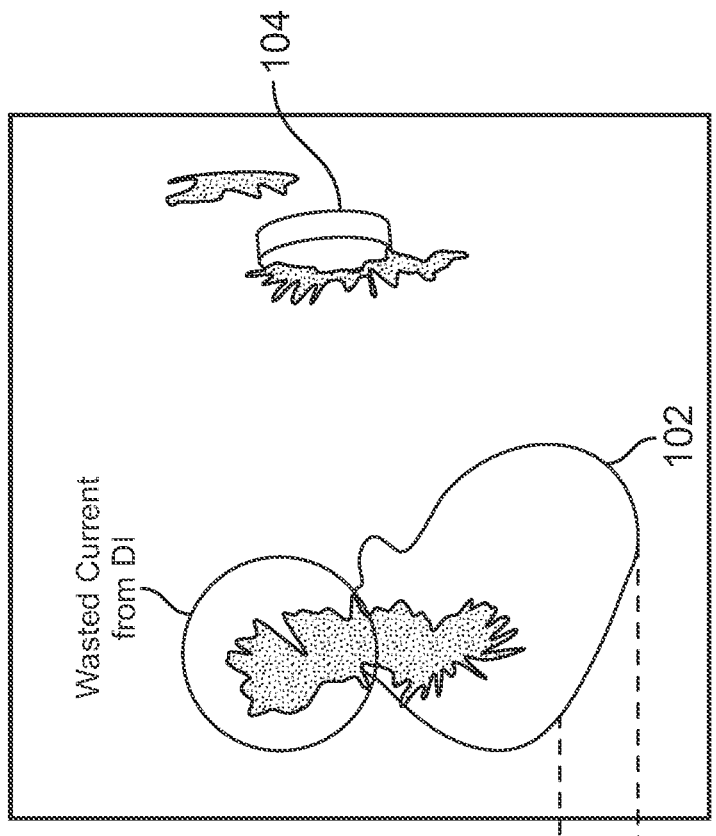
FIGS. 9A and 9B are conceptual illustrations of MRI images of a patient's heart in a supine posture (FIG. 9A) and an upright posture (FIG. 9B) during inhalation along with an EV ICD.
Figure 9A:
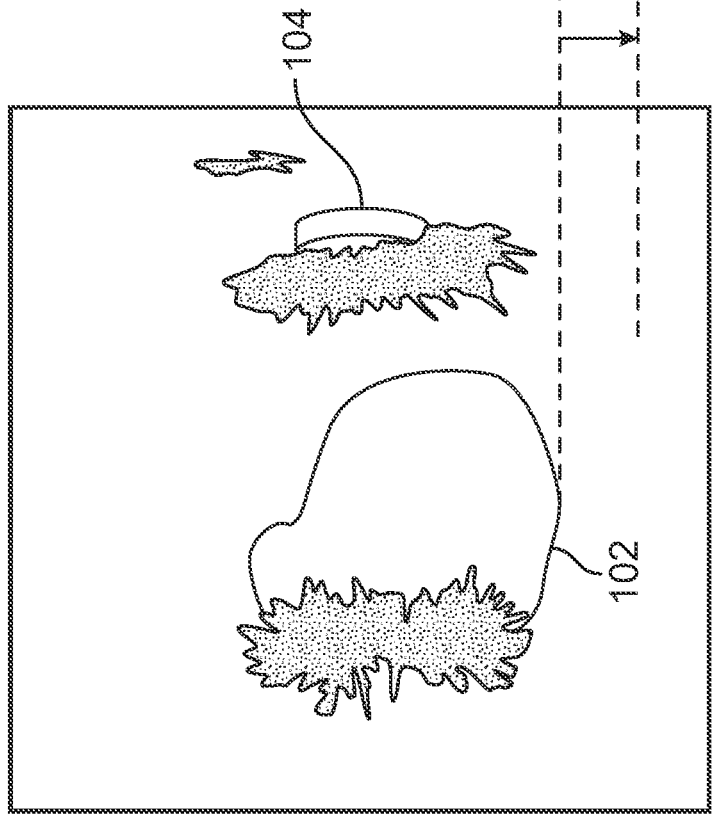

FIGS. 9A and 9B are conceptual illustrations of MRI images of a patient's heart 102 in a supine posture (FIG. 9A) and an upright posture (FIG. 9B) during inhalation along with an EV ICD 104. The shaded areas in both FIGS. 9A and 9B indicate areas of high current density from the delivery of defibrillation therapy using defibrillation vector D1, which includes a housing electrode in combination with at least one lead electrode. As shown, upon standing and during inhalation, heart 102 moved cadually as indicated by the arrow between the images. In some examples, this may result in the defibrillation vector D1 becoming less effective during defibrillation. As such, for some cases, the defibrillation efficacy may be improved by sensing the upright posture and, in response to sensing the upright posture, disabling a vector (e.g., vector D1), increasing the defibrillation energy, or both.

Figure 10:
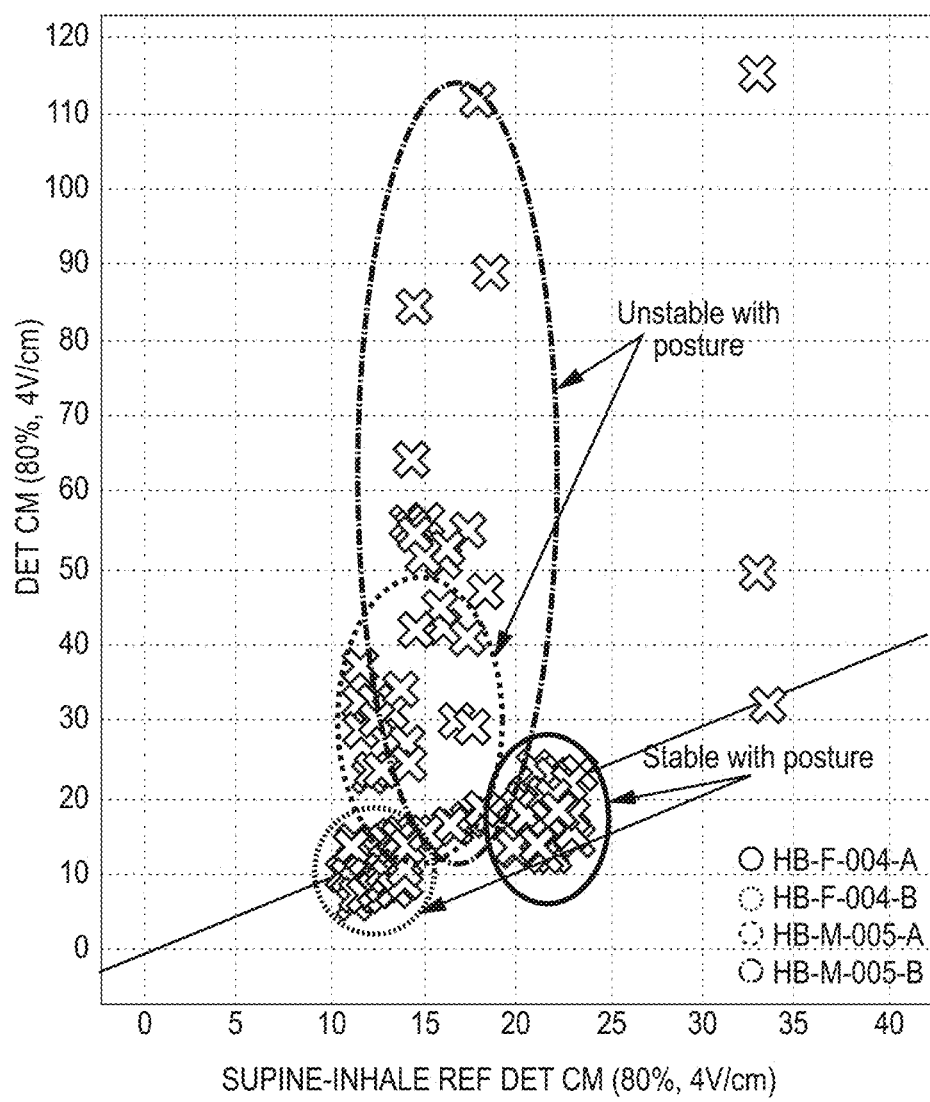
FIG. 10 is a graph illustrating DFT variation with posture and respiration for a variety of modelled patients.

FIG. 10 is a graph illustrating DFT variation with posture and respiration for a variety of modelled patients. The stability graph compares defibrillation threshold (DFT) in the supine, inhalation case (X axis) with the value in all other postures (Y axis). For some patients (HB-F-004-A and HB-F-004-B) the DFT was stable versus posture while for others (HB-M-005-A and HB-M-005-B) it may vary widely. It was believed that patients with an unstable DFT may benefit from a device that increases shock energy when the patient is sensed to be in a posture that has been determined to be problematic.

Various aspects of the disclosure have been described. These and other aspects are within the scope of the following claims and clauses.

Clause 1. A method for controlling delivery of anti-tachyarrhythmia shock therapy by a medical device system comprising a plurality of electrodes for delivering the anti-tachyarrhythmia shock therapy, the method comprising storing, in a memory of the medical device system, a respective value for each of a plurality of anti-tachyarrhythmia shock therapy parameters and, in association with each of a plurality of heart position states, a respective modification of at least one of the anti-tachyarrhythmia shock therapy parameters; and by processing circuitry of the medical device system determining a current one of the plurality of heart position states of a patient; modifying the at least one anti-tachyarrhythmia shock therapy parameter value according to the modification associated with the current heart position state; and controlling the delivery of the anti-tachyarrhythmia shock therapy according to the modified at least one anti-tachyarrhythmia shock therapy parameter value.

Clause 2. The method of clause 1, further comprising delivering, by therapy delivery circuitry of the medical device system, the anti-tachyarrhythmia shock therapy according to the modified at least one anti-tachyarrhythmia shock therapy parameter value.

Clause 3. The method of clause 1 or 2, wherein the medical device system comprises a medical electrical lead comprising a proximal end coupled to an implantable cardioverter-defibrillator, and a distal portion including the at least one of the plurality of electrodes and implanted substantially within an anterior mediastinum of the patient.

Clause 4. The method of any of clauses 1 to 3, wherein the plurality of heart position states comprises a plurality of postures of the patient.

Clause 5. The method of any of clauses 1 to 4, wherein determining the current heart position state of the patient comprises determining at least one of a respiratory phase, a respiratory rate, or a respiratory depth of the patient.

Clause 6. The method of any of clauses 1 to 5, wherein modifying the at least one anti-tachyarrhythmia shock therapy parameter value comprises modifying a tachyarrhythmia detection parameter.

Clause 7. The method of clause 6, wherein modifying the tachyarrhythmia detection parameter comprises modifying a cardiac electrogram sensing amplitude threshold.

Clause 8. The method of any of clauses 1 to 7, wherein modifying the at least one anti-tachyarrhythmia shock therapy parameter value comprises modifying an anti-tachyarrhythmia shock magnitude.

Clause 9. The method of any of clauses 1 to 8, wherein the plurality of anti-tachyarrhythmia shock therapy parameters comprises a sensing vector comprising at least two of the plurality of electrodes and a shock vector comprising at least two of the plurality of electrodes, and wherein modifying the at least one anti-tachyarrhythmia shock therapy parameter value comprises modifying at least one of the sensing vector or the shock vector.

Clause 10. The method of clause 9, wherein modifying at least one of the sensing vector or the shock vector comprises removing one of the at least two of the plurality of electrodes from the at least one of the sensing vector or the shock vector.

Clause 11. The method of clause 10, wherein removing the one of the at least two of the plurality of electrodes comprises removing a most superior one of the at least two of the plurality of electrodes.

Clause 12. The method of clause 11, wherein the distal portion of the medical electrical lead includes the at least two of the plurality of electrodes, and wherein removing a most superior one of the at least two of the plurality of electrodes comprises removing a most distal one of the at least two of the plurality of electrodes.

Clause 13. The method of clause 11, wherein determining the heart position state of the patient comprises at least one of determining that the patient is in an upright posture; or determining that a respiratory state of the patient comprises at least one of an inhalation phase, a respiratory depth satisfying a respiratory depth threshold, or a respiratory rate satisfying a respiratory rate threshold.

Clause 14. A medical device system for delivering anti-tachyarrhythmia shock therapy, the system comprising: a plurality of electrodes; a memory configured to store a respective value for each of a plurality of anti-tachyarrhythmia shock therapy parameters and, in association with each of a plurality of heart position states, a respective modification of at least one of the anti-tachyarrhythmia shock therapy parameters; and processing circuitry configured to: determine a current one of the plurality of heart position states of the patient; modify the at least one anti-tachyarrhythmia shock therapy parameter value according to the modification associated with the current heart position state; and control the delivery of the anti-tachyarrhythmia shock therapy via the electrodes according to the modified at least one anti-tachyarrhythmia shock therapy parameter value.

Clause 15. The medical device system of clause 14, further comprising therapy delivery circuitry configured to deliver the anti-tachyarrhythmia shock therapy via the electrodes according to the modified at least one anti-tachyarrhythmia shock therapy parameter value.

Clause 16. The medical device system of clause 14 or 15, further comprising: an implantable cardioverter-defibrillator; and a medical electrical lead comprising a proximal end coupled to the implantable cardioverter-defibrillator and a distal portion including the at least one of the plurality of electrodes configured for implantation substantially within an anterior mediastinum of the patient.

Clause 17. The medical device system of any of clauses 14 to 16, wherein the plurality of heart position states comprises a plurality of postures.

Clause 18. The medical device system of any of clauses 14 to 17, wherein the processing circuitry is configured to determine the current heart position state of the patient by at least determining at least one of a respiratory phase, a respiratory rate, or a respiratory depth of the patient.

Clause 19. The medical device system of any of clauses 14 to 18, wherein the processing circuitry is configured to modify the at least one anti-tachyarrhythmia shock therapy parameter value by at least modifying a tachyarrhythmia detection parameter.

Clause 20. The medical device system of clause 19, wherein the processing circuitry is configured to modify the tachyarrhythmia detection parameter by at least modifying a cardiac electrogram sensing amplitude threshold.

Clause 21. The medical device system of any of clauses 14 to 20, wherein the processing circuitry is configured to modify the at least one anti-tachyarrhythmia shock therapy parameter value by at least modifying an anti-tachyarrhythmia shock magnitude.

Clause 22. The medical device system of any of clauses 14 to 21, wherein the plurality of anti-tachyarrhythmia shock therapy parameters comprises a sensing vector comprising at least two of the plurality of electrodes and a shock vector comprising at least two of the plurality of electrodes, and wherein the processing circuitry is configured to modify the at least one anti-tachyarrhythmia shock therapy parameter value by at least modifying at least one of the sensing vector or the shock vector.

Clause 23. The medical device system of clause 22, wherein the processing circuitry is configured to modify at least one of the sensing vector or the shock vector by at least removing one of the at least two of the plurality of electrodes from the at least one of the sensing vector or the shock vector.

Clause 24. The medical device system of clause 23, wherein the processing circuitry is configured to remove the one of the at least two of the plurality of electrodes by at least removing a most superior one of the at least two of the plurality of electrodes.

Clause 25. The medical device system of clause 24, wherein the distal portion of the medical electrical lead includes the at least two of the plurality of electrodes, and wherein the processing circuitry is configured to remove a most superior one of the at least two of the plurality of electrodes by at least removing a most distal one of the at least two of the plurality of electrodes.

Clause 26. The medical device system of clause 24, wherein the processing circuitry is configured to determine the heart position state of the patient by at least one of: determining that the patient is in an upright posture; or determining that a respiratory state of the patient comprises at least one of an inhalation phase, a respiratory depth satisfying a respiratory depth threshold, or a respiratory rate satisfying a respiratory rate threshold.

Clause 27. A method for controlling cardiac electrogram sensing or delivery of cardiac therapy by an implantable medical device system comprising a plurality of electrodes, the method comprising, by processing circuitry of the medical device system: determining a heart position state of the patient; modifying a vector comprising at least two of the plurality of electrodes based on the determined heart position state; and controlling the medical device system to at least sense a cardiac electrogram or deliver cardiac therapy via the modified vector comprising the at least two of the plurality of electrodes.

Clause 28. The method of clause 27, further comprising delivering, by therapy delivery circuitry of the medical device system, the cardiac therapy via the modified vector comprising the at least two of the plurality of electrodes.

Clause 29. The method of clause 27 or 28, wherein the medical device system comprises a medical electrical lead including a proximal end coupled to an implantable medical device, and a distal portion including the at least two of the plurality of electrodes and implanted substantially within an anterior mediastinum of the patient.

Clause 30. The method of clause 29, wherein the implantable medical device comprises an implantable cardioverter-defibrillator and the plurality of electrodes comprises a plurality of electrodes for delivering anti-tachyarrhythmia shock therapy, wherein the cardiac therapy comprises the anti-tachyarrhythmia shock therapy, and wherein controlling the medical device system to deliver cardiac therapy via the modified vector comprising the at least two of the plurality of electrodes comprises controlling the medical device system to deliver the anti-tachyarrhythmia shock therapy.

Clause 31. The method of clause 29, wherein the cardiac therapy comprises cardiac pacing, and wherein controlling the medical device system to deliver cardiac therapy via the modified vector comprising the at least two of the plurality of electrodes comprises controlling the medical device system to deliver the cardiac pacing.

Clause 32. The method of any of clauses 27 to 31, wherein the plurality of heart position states comprises a plurality of postures of the patient.

Clause 33. The method of any of clauses 27 to 32, wherein determining the current heart position state of the patient comprises determining at least one of a respiratory phase, a respiratory rate, or a respiratory depth of the patient.

Clause 34. The method of any of clauses 27 to 32, wherein modifying the vector comprising at least two of the plurality of electrodes based on the determined heart position state comprises removing one of the at least two of the plurality of electrodes from the vector.

Clause 35. The method of clause 34, wherein removing the one of the at least two of the plurality of electrodes from the vector comprises removing a most superior one of the at least two of the plurality of electrodes.

Clause 36. The method of clause 35, wherein determining the heart position state of the patient comprises at least one of: determining that the patient is in an upright posture; or determining that a respiratory state of the patient comprises at least one of an inhalation phase, a respiratory depth satisfying a respiratory depth threshold, or a respiratory rate satisfying a respiratory rate threshold.

Clause 37. The method of any of clauses 27-36, the method further comprising: storing, in a memory of the medical device system, a respective value for each of a plurality of cardiac therapy parameters and in association with each of a plurality of heart position states, a respective modification of at least one of the cardiac therapy parameters; and modifying the at least one cardiac therapy parameter value according to the modification associated with the heart position state of the patient, wherein controlling the medical device system to at least deliver the cardiac therapy via the modified vector comprising the at least two of the plurality of electrodes comprises controlling the delivery of the cardiac therapy according to the modified at least one cardiac therapy parameter value.

Clause 38. The method of clause 37, wherein the modifying the at least one cardiac therapy parameter value comprises modifying a tachyarrhythmia detection parameter.

Clause 39. The method of clause 38, wherein modifying the tachyarrhythmia detection parameter comprises a cardiac electrogram sensing amplitude threshold.

Clause 40. The method of clause 37, wherein modifying the at least one cardiac therapy parameter value comprises modifying an anti-tachyarrhythmia shock magnitude.

Clause 41. The method of clause 37, wherein modifying the at least one cardiac therapy parameter value comprises modifying an anti-tachyarrhythmia pacing parameter.

Clause 42. A medical device system for controlling cardiac electrogram sensing or delivery of cardiac therapy, the system comprising, a plurality of electrodes; and processing circuitry configured to: determine a heart position state of the patient; modify a vector comprising at least two of the plurality of electrodes based on the determined heart position state; and control the medical device system to at least sense a cardiac electrogram or deliver cardiac therapy via the modified vector comprising the at least two of the plurality of electrodes.

Clause 43. The medical device system of clause 42, further comprising delivering, by therapy delivery circuitry of the medical device system, the cardiac therapy via the modified vector comprising the at least two of the plurality of electrodes.

Clause 44. The medical device system of clause 42 or 43, wherein the medical device system comprises a medical electrical lead including a proximal end coupled to an implantable medical device, and a distal portion including the at least two of the plurality of electrodes and implanted substantially within an anterior mediastinum of the patient.

Clause 45. The medical device system of clause 44, wherein the implantable medical device comprises an implantable cardioverter-defibrillator and the plurality of electrodes comprises a plurality of electrodes for delivering anti-tachyarrhythmia shock therapy, wherein the cardiac therapy comprises the anti-tachyarrhythmia shock therapy, and wherein controlling the medical device system to deliver cardiac therapy via the modified vector comprising the at least two of the plurality of electrodes comprises controlling the medical device system to deliver the anti-tachyarrhythmia shock therapy.

Clause 46. The medical device system of clause 44, wherein the plurality of electrodes comprises a plurality of electrodes for delivering cardiac pacing wherein the cardiac therapy comprises anti-arrhythmia pacing, and wherein controlling the medical device system to deliver cardiac therapy via the modified vector comprising the at least two of the plurality of electrodes comprises controlling the medical device system to deliver the anti-arrhythmia pacing.

Clause 47. The medical device system of any of clauses 42 to 46, wherein the plurality of heart positions comprises a plurality of postures.

Clause 48. The medical device system of any of clauses 42 to 47, wherein determining the current heart position state of the patient comprises determining at least one of a respiratory phase, a respiratory rate, or a respiratory depth of the patient.

Clause 49. The medical device system of any of clauses 42 to 47, wherein modifying the vector comprising at least two of the plurality of electrodes based on the determined heart position state comprises removing one of the at least two of the plurality of electrodes from the vector.

Clause 50. The medical device system of clause 49, wherein removing the one of the at least two of the plurality of electrodes from the vector comprises removing a most superior one of the at least two of the plurality of electrodes.

Clause 51. The medical device system of clause 50, wherein determining the heart position state of the patient comprises at least one of: determining that the patient is in an upright posture; or determining that a respiratory state of the patient comprises at least one of an inhalation phase, a respiratory depth satisfying a respiratory depth threshold, or a respiratory rate satisfying a respiratory rate threshold.

Clause 52. The medical device system of any of clauses 42-51, further comprising a memory, wherein the processing circuitry is further configured to: store, in the memory, a respective value for each of a plurality of cardiac therapy parameters and in association with each of a plurality of heart position states, a respective modification of at least one of the cardiac therapy parameters; and modify the at least one cardiac therapy parameter value according to the modification associated with the heart position state of the patient, wherein the processing circuitry is configured to control the implantable medical device to at least deliver the cardiac therapy via the modified vector comprising the at least two of the plurality of electrodes by at least controlling the delivery of the cardiac therapy according to the modified at least one cardiac therapy parameter value.

Clause 53. The medical device system of clause 52, wherein the processing circuitry is configured to modify the at least one cardiac therapy parameter value by at least modifying a tachyarrhythmia detection parameter.

Clause 54. The medical device system of clause 53, wherein the processing circuitry is configured to modify the tachyarrhythmia detection parameter by at least modifying a cardiac electrogram sensing amplitude threshold.

Clause 55. The medical device system of clause 52, wherein the processing circuitry is configured to modify the at least one cardiac therapy parameter value by at least modifying an anti-tachyarrhythmia shock magnitude.

Clause 56. The medical device system of clause 52, wherein the processing circuitry is configured to modify the at least one cardiac therapy parameter value by at least modifying an anti-tachyarrhythmia pacing parameter.

Clause 57. A method comprising any method described herein, or any combination of the methods described herein.

Clause 58. A method comprising any combination of the methods of clauses 1-13 and 27-41.

Clause 59. A system comprising means for performing the method of any of clauses 1-13, 27-41, 57 or 58.

Clause 60. A non-transitory computer-readable storage medium comprising instructions stored thereon that, when executed by processing circuitry cause the processing circuitry to perform the method of any of clauses 1-13, 27-41, 57 or 58.

What is claimed is:

1. A method for controlling delivery of anti-tachyarrhythmia shock therapy by a medical device system comprising a plurality of electrodes for delivering the anti-tachyarrhythmia shock therapy, the method comprising:
   receiving a first indication of a respective value for each of a plurality of anti-tachyarrhythmia shock therapy parameters;
   storing, in a memory of the medical device system, the respective value for each of the plurality of anti-tachyarrhythmia shock therapy parameters;
   receiving a second indication of a first modification to at least one of the anti-tachyarrhythmia shock therapy parameters for a first heart position state, and a second modification to the at least one of the anti-tachyarrhythmia shock therapy parameters for a second heart position state, wherein the second heart position state is different than the first heart position state;
   storing, in association with the first heart position state, the first modification of the at least one of the anti-tachyarrhythmia shock therapy parameters;
   storing, in association with the second heart position state, the second modification of the at least one of the anti-tachyarrhythmia shock therapy parameters, wherein the second modification is different from the first modification; and
   by processing circuitry of the medical device system:
      determining, using sensing circuitry, a current heart position state of a patient is the first heart position state;
      modifying, based at least in part on the determination of the current heart position state being the first heart position state, the at least one anti-tachyarrhythmia shock therapy parameter value according to the modification associated with the first heart position state stored in the memory, wherein modifying the at least one anti-tachyarrhythmia shock therapy parameter value comprises increasing or decreasing an anti-tachyarrhythmia shock magnitude; and
      controlling delivery of the anti-tachyarrhythmia shock therapy to the patient according to the modified at least one anti-tachyarrhythmia shock therapy parameter value associated with the first heart position state.

2. The method of claim 1, further comprising delivering, by therapy delivery circuitry of the medical device system, the anti-tachyarrhythmia shock therapy according to the modified at least one anti-tachyarrhythmia shock therapy parameter value associated with the first heart position state.

3. The method of claim 1, wherein the medical device system comprises a medical electrical lead comprising a proximal end coupled to an implantable cardioverter-defibrillator, and a distal portion including the at least one of the plurality of electrodes and implanted substantially within an anterior mediastinum of the patient.

4. The method of claim 1, wherein the first heart position state comprises a first posture of the patient and the second heart position state comprises a second posture of the patient different from the first posture.

5. The method of claim 1, wherein determining the current heart position state of the patient is the first heart position state comprises determining that at least one of a respiratory phase, a respiratory rate, or a respiratory depth of the patient satisfies at least one of a presence of a specific respiratory phase, a respiratory rate threshold, or a respiratory depth threshold.

6. The method of claim 1, wherein modifying the at least one anti-tachyarrhythmia shock therapy parameter value comprises modifying a tachyarrhythmia detection parameter.

7. The method of claim 6, wherein modifying the tachyarrhythmia detection parameter comprises modifying a cardiac electrogram sensing amplitude threshold.

8. The method of claim 1, wherein determining the current heart position state of the patient is the first heart position state comprises determining a current posture of the patient and a current respiration state of the patient.

9. The method of claim 1, further comprising, by processing circuitry of the medical device system:
   subsequently determining, using sensing circuitry, the current heart position state of the patient is the second heart position state;
   modifying, based at least in part on the determination of the current heart position state being the second heart position state, the at least one anti-tachyarrhythmia shock therapy parameter value according to the modification associated with the second heart position state stored in the memory, wherein modifying the at least one anti-tachyarrhythmia shock therapy parameter value comprises at least one of modifying an anti-tachyarrhythmia shock magnitude, modifying a sensing vector, or modifying a shock vector; and controlling delivery of the anti-tachyarrhythmia shock therapy to the patient according to the modified at least one anti-tachyarrhythmia shock therapy parameter value associated with the second heart position state.

10. The method of claim 1, wherein determining the current heart position state of the patient is the first heart position state comprises determining a posture and a respiratory state of the patient.

11. A medical device system for delivering anti-tachyarrhythmia shock therapy, the system comprising:
a plurality of electrodes;
a memory configured to:
store a respective value for each of a plurality of anti-tachyarrhythmia shock therapy parameters,
a first modification of at least one of the anti-tachyarrhythmia shock therapy parameters for a first heart position state, and
a second modification to the at least one of the anti-tachyarrhythmia shock therapy parameters for a second heart position state, wherein the second heart position state is different than the first heart position state, wherein the second modification is different from the first modification; and
processing circuitry configured to:
receive a first indication of the respective value for each of the plurality of anti-tachyarrhythmia shock therapy parameters,
receive a second indication of the first modification of the at least one of the anti-tachyarrhythmia shock therapy parameters for the first heart position state, and the second modification to the at least one of the anti-tachyarrhythmia shock therapy parameters for the second heart position state;
determine, using sensing circuitry, a current heart position state of a patient is the first heart position state;
modify, based at least in part on the determination of the current heart position state being the first heart position state, the at least one anti-tachyarrhythmia shock therapy parameter value according to the modification associated with the first heart position state stored in the memory, wherein the processing circuitry is configured to modify the at least one anti-tachyarrhythmia shock therapy parameter value by increasing or decreasing an anti-tachyarrhythmia shock magnitude; and
control delivery of the anti-tachyarrhythmia shock therapy via the electrodes according to the modified at least one anti-tachyarrhythmia shock therapy parameter value associated with the first heart position state.

12. The medical device system of claim 11, further comprising therapy delivery circuitry configured to deliver the anti-tachyarrhythmia shock therapy via the electrodes according to the modified at least one anti-tachyarrhythmia shock therapy parameter value associated with the first heart position state.

13. The medical device system of claim 11, further comprising:
an implantable cardioverter-defibrillator; and
a medical electrical lead comprising a proximal end coupled to the implantable cardioverter-defibrillator and a distal portion including the at least one of the plurality of electrodes configured for implantation substantially within an anterior mediastinum of the patient.

14. The medical device system of claim 11, wherein the first heart position state comprises a first posture of the patient and the second heart position state comprises a second posture of the patient different from the first posture.

15. The medical device system of claim 11, wherein the processing circuitry is configured to determine that the current heart position state of the patient is the first heart position state by at least determining at least one of a respiratory phase, a respiratory rate, or a respiratory depth of the patient satisfies at least one of a presence of a specific respiratory phase, a respiratory rate threshold, or a respiratory depth threshold.

16. The medical device system of claim 11, wherein the processing circuitry is configured to modify the at least one anti-tachyarrhythmia shock therapy parameter value by at least modifying a tachyarrhythmia detection parameter.

17. The medical device system of claim 16, wherein the processing circuitry is configured to modify the tachyarrhythmia detection parameter by at least modifying a cardiac electrogram sensing amplitude threshold.

18. The medical device system of claim 11, wherein the processing circuitry is configured to determine the current heart position state of the patient is the first heart position state by at least one of:
determining that the patient is in an upright posture; or
determining that a respiratory state of the patient comprises at least one of an inhalation phase, a respiratory depth satisfying a respiratory depth threshold, or a respiratory rate satisfying a respiratory rate threshold.

19. The medical device system of claim 11, wherein the processing circuitry is configured to determine the current heart position state of the patient is the first heart position state by at least determining a current posture of the patient and a current respiration state of the patient.

20. The medical device system of claim 11, wherein the processing circuitry is configured to:
subsequently determine, using sensing circuitry, the current heart position state of the patient is the second heart position state;
modify, based at least in part on the determination of the current heart position state being the second heart position state, the at least one anti-tachyarrhythmia shock therapy parameter value according to the modification associated with the second heart position state stored in the memory, wherein the processing circuitry is configured to modify the at least one anti-tachyarrhythmia shock therapy parameter value by at least one of modifying an anti-tachyarrhythmia shock magnitude, modifying a sensing vector, or modifying a shock vector; and
control delivery of the anti-tachyarrhythmia shock therapy via the electrodes according to the modified at least one anti-tachyarrhythmia shock therapy parameter value associated with the second heart position state.

21. The medical device system of claim 11, wherein the processing circuitry is configured to determine that the current heart position state of the patient is the first heart position state by at least determining a posture and a respiratory state of the patient.

22. A method for controlling delivery of cardiac therapy by an implantable medical device system comprising a plurality of electrodes, the method comprising, by processing circuitry of the medical device system:
   determining, using sensing circuitry, a current heart position state of a patient is a first heart position state rather than a second heart position state, wherein determining the current heart position state of the patient is the first heart position state rather than the second heart position state comprises determining at least one of a respiratory phase, a respiratory rate, or a respiratory depth of the patient;
   modifying, based at least in part on the determined at least one of the respiratory phase, the respiratory rate, or the respiratory depth of the patient, a vector comprising at least two of the plurality of electrodes based on the determined current heart position state being the first heart position state;
   modifying, based at least in part on the determination of the current heart position state being the first heart position state, at least one anti-tachyarrhythmia shock therapy parameter value by increasing or decreasing an anti-tachyarrhythmia shock magnitude; and
   controlling the medical device system to deliver anti-tachyarrhythmia shock therapy via the modified vector comprising the at least two of the plurality of electrodes and according to the modified at least one anti-tachyarrhythmia shock therapy parameter value associated with the first heart position state.

23. A method for controlling delivery of anti-tachyarrhythmia shock therapy by a medical device system comprising a plurality of electrodes for delivering the anti-tachyarrhythmia shock therapy, the method comprising:

receiving a first indication of a respective value for each of a plurality of anti-tachyarrhythmia shock therapy parameters;
storing, in a memory of the medical device system, the respective value for each of the plurality of anti-tachyarrhythmia shock therapy parameters;
receiving a second indication of a first modification to at least one of the anti-tachyarrhythmia shock therapy parameters for a first heart position state;
storing, in association with the first heart position state, the first modification of the at least one of the anti-tachyarrhythmia shock therapy parameters; and
by processing circuitry of the medical device system:
   determining, using sensing circuitry, a current heart position state of a patient is the first heart position state;
   modifying, based at least in part on the determination of the current heart position state being the first heart position state, the at least one anti-tachyarrhythmia shock therapy parameter value according to the modification associated with the first heart position state stored in the memory, wherein modifying the at least one anti-tachyarrhythmia shock therapy parameter value comprises increasing or decreasing an anti-tachyarrhythmia shock magnitude; and
   controlling delivery of the anti-tachyarrhythmia shock therapy to the patient according to the modified at least one anti-tachyarrhythmia shock therapy parameter value associated with the first heart position state.

* * * * *